United States Patent
Sun et al.

(10) Patent No.: US 7,625,572 B2
(45) Date of Patent: Dec. 1, 2009

(54) TRANSFORMED BACTERIUM LACKING SELECTABLE MARKER AND OVEREXPRESSION OF ANTIGENS IN MYCOBACTERIA

(75) Inventors: Ronggai Sun, Ellicott City, MD (US); David Michael Hone, Rockville, MD (US); Jerald C. Sadoff, Washington, DC (US)

(73) Assignee: Aeras Global TB Vaccine Foundation, Bethesda, MD (US)

( * ) Notice: Subject to any disclaimer, the term of this patent is extended or adjusted under 35 U.S.C. 154(b) by 277 days.

(21) Appl. No.: 11/288,424

(22) Filed: Nov. 29, 2005

(65) Prior Publication Data

US 2006/0121054 A1 Jun. 8, 2006

Related U.S. Application Data

(60) Provisional application No. 60/631,977, filed on Dec. 1, 2004.

(51) Int. Cl.
*A61K 39/04* (2006.01)
*A61K 39/02* (2006.01)
*A61K 39/12* (2006.01)
(52) U.S. Cl. ............ 424/248.1; 424/9.1; 424/9.2; 424/93.2; 424/184.1; 424/200.1; 424/234.1; 435/173.6; 435/466; 435/471; 435/476

(58) Field of Classification Search ............ 424/9.1, 424/9.2, 93.2, 184.1, 200.1, 243.1, 248.1; 435/173.6, 440, 461, 466, 471, 476
See application file for complete search history.

(56) References Cited

U.S. PATENT DOCUMENTS

| 5,736,367 | A | * | 4/1998 | Haun et al. | 435/252.3 |
| 5,783,386 | A | * | 7/1998 | Jacobs et al. | 435/6 |
| 6,004,815 | A | * | 12/1999 | Portnoy et al. | 435/454 |
| 6,423,545 | B1 | | 7/2002 | Pavelka, Jr. et al. | |
| 6,562,348 | B2 | * | 5/2003 | Hondalus et al. | 424/200.1 |

OTHER PUBLICATIONS

Dubnau, E., "overproduction of mycobacterial ribosomal protein S13 induces catalase/peroxidase activity and hypersensitivity to isoniazid in *Mycobacterium smegmatis*". Gene, vol. 170, pp. 17-22, 1996.*
S. Snapper, et al; Lysogeny and Transformation in Mycobacteria: Stable expressino of foreign genes; Proc. Natl. Acad. Scie. USA; vol. 85; pp. 6987-6991; Sep. 1988.

* cited by examiner

*Primary Examiner*—Rodney P. Swartz
(74) *Attorney, Agent, or Firm*—Whitham Curtis Christofferson & Cook, PC (57) ABSTRACT

Recombinant *Mycobacterium* strains with improved vaccinal properties for use as vaccinating agents are provided. The parent strains of the recombinant *Mycobacterium* strains are selected for their potent immunogenicity. The *Mycobacterium* strains do not display antibiotic resistance, and do not exhibit horizontal transfer to gram-negative bacteria.

29 Claims, 5 Drawing Sheets

TRANSFORMED BACTERIUM LACKING SELECTABLE MARKER AND OVEREXPRESSION OF ANTIGENS IN MYCOBACTERIA

This application claims benefit of U.S. provisional patent application No. 60/631,977, filed Dec. 1, 2004, the complete contents of which are hereby incorporated by reference.

BACKGROUND OF THE INVENTION

1. Field of the Invention

The invention provides *Mycobacterium* strains with improved vaccinal properties for use as vaccinating agents against tuberculosis. The *Mycobacterium* strains are preferably selected from parent strains that are identified as having potent immunogenicity, do not display antibiotic resistance, and do not exhibit horizontal transfer to gram-negative bacteria. The invention also provides *Mycobacterium* with improved properties for delivering transgenes that will have vaccinal properties for use in vaccinating against other diseases and for use in the treatment of cancer.

2. Background

*Mycobacterium tuberculosis* (M. tb) has infected one-third of the world's population, causing active disease in 8 million and killing 1.6-2.2 million individuals every year, most of whom live in the developing world. Tuberculosis (TB) is an epidemic of global proportions that is growing and becoming even more deadly as it intersects with the spread of HIV. TB is the number one killer of people with AIDS.

BCG, the current widely used TB vaccine, was developed over 80 years ago and when tested has had widely variable rates of efficacy against pulmonary tuberculosis, including no efficacy in the last large field trial conducted in India (Fine et al., Vaccine, 16(20):1923-1928; 1998; Anonymous, Indian J Med Res., Aug; 110:56-69; 1999. Nonetheless, the World Health Organization currently recommends BCG at birth or first contact with health services for all children (except those with symptoms of HIV disease/AIDS) in high TB prevalent countries. This policy is based on evidence that BCG protects against serious childhood forms of TB (Lanckriet et al., Int J Epidemiol, 24(5): 1042-1049; 1995; Rodrigues et al., J Epidemiol Community Health 45(1): 78-80; 1991. Protection by BCG against TB beyond early childhood is a controversial subject with limited data giving mixed results. The high incidence of pediatric and adult TB in developing countries where infant BCG immunization is widely practiced, however, indicates that BCG as currently administered is not highly efficacious over the many years when people are at risk of TB disease. Thus, BCG is considered to be an inadequate public health tool for the intervention and control of TB.

Approximately 70 percent of humans exposed to TB organisms, and who have normal immune systems, do not become infected, and of those that do become infected only about 5 percent develop disease within the first two years. The majority of infected individuals suppress the infection, which is associated with the development of robust cellular immune responses to M. tb antigens. An additional 5 percent later reactivate when immunity declines. Both primary and reactivation disease are much more common in people with HIV/AIDS, again emphasizing the role of immunity in preventing and controlling infection.

SUMMARY OF THE INVENTION

Because most humans are able to control TB, there is good reason to hope that by inducing long lasting immunity of the appropriate kind it should be possible to develop effective vaccines that prevent initial infection after exposure, prevent early progression to disease, prevent reactivation from the latent state and prevent relapse after treatment. Ultimately, it is the combination of systematic vaccine use plus chemotherapeutic intervention that will eventually eliminate M. tb as a human pathogen.

In light of the critical role childhood BCG vaccination is thought to play in preventing acute TB, it is difficult to replace BCG in trials to evaluate candidate TB vaccines without overwhelming evidence that the new TB vaccine is a superior product. The problem is that M. tb is primarily a human-specific pathogen and animal models only mimic parts of the host-pathogen interaction. Thus, definitive evidence that a new TB vaccine possesses improved potency can only be obtained from controlled field trials in humans. These considerations lead many investigators to conclude that a key step toward an improved TB vaccine will be to develop improved strains of BCG, and animal models, despite their limitations, suggest that recombinant BCG's that over-express protective antigens have increased potency compared to BCG.

Certain M. tb antigens possess vaccinal properties and, when given to animals as vaccine formulations, impart protection that is similar to that achieved by BCG alone (Anderson, Infect Immun 62(6) 2536-2544; 1994). To move these candidates forward, a strategy was developed to enhance the immunogenicity of such antigens in BCG. Thus, BCG strains were developed that over-express selected M. tb antigens and these recombinant BCG (rBCG) strains were shown to induce stronger protection compared to the parental BCG strains from which the rBCG strain was derived (Horwitz et al., Infect Immun 72(4): 1672-1679; 2003). In one study, a rBCG strain that expressed antigen 85B (herein referred to as "Ag85B") proved to be more efficacious than BCG mixed with the same antigen (Horwitz et al., supra, 2003). Based on these findings this approach has tremendous potential.

In certain circumstances BCG strains that over-express antigens may be used to safely and effectively elicit immune responses that confer protection from infection by TB.

The present invention provides genetically engineered (recombinant) *Mycobacterium* strains with improved vaccinal properties for use as vaccinating agents against tuberculosis. They possess a variety of features, each of which serves to increase the immunogenicity of the strains. Recombinant *Mycobacterium* strains of the present invention are developed from parent strains that are purposefully selected for their potent immunogenicity. In other words, the strain of *Mycobacterium* that is selected as a parent strain to undergo genetic manipulation (for example, to overexpress a tuberculosis antigen) is chosen because, even prior to the genetic manipulation, it exhibits the ability to elicit a potent immune response in a vaccinated host. BCG strain Danish 1331 is an example. Such strains are then preferably modified, for example, to overexpress a tuberculosis antigen of interest. Preferably, a promoter that is in vivo activated is used in the genetically recombinant mycobacterium. In addition, the recombinant *Mycobacterium* strains of the present invention are genetically engineered to be selectable on a basis other than by antibiotic resistance or are constructed in such a way that they need no selective markers at all, making them generally safe for use as vaccinating agents in human populations. As an example, a gene required for *Mycobacterial* replication is removed and placed in an expression plasmid. In addition, the recombinant *Mycobacterium* strains of the present invention do not undergo horizontal transfer to gram-negative bacteria and are thus incapable of "escaping" from the host organism. This also ensures their safety as vaccine agents in human populations.

As another example, the present invention describes the use of Antigen 85b expression by plasmids as a plasmid stabilization factor, which obviates the need for antibiotic selection for their maintenance. Direct transformation of *Mycobacterial* strains with high concentrations of minimal plasmids expressing Ag85B plus other antigens utilizing PCR positive selection for their identification yields *Mycobacterial* strains overexpressing antigens with plasmid stability in the absence of antibiotic or auxotrophic selection. In addition, while the recombinant *Mycobacterium* strains of the present invention are excellent agents for use in tuberculosis vaccines, they may also be genetically engineered to express or over-express antigens other than those relevant to tuberculosis, and are thus useful as vaccine agents against other diseases as well. Furthermore, rBCG over expressing TB antigens or antigens important in other diseases can be used in prime boost regimens with recombinant proteins, together with adjuvants, recombinant viral vectors, or DNA or RNA vaccines as boosters.

The invention provides a transformed bacterium or progeny thereof, which incorporates a foreign nucleotide sequence which replicates and is expressed in the transformed bacterium (or progeny), wherein the foreign nucleotide sequence is not linked to a selectable marker. In one embodiment, the foreign nucleotide sequence resides on a plasmid, and in some embodiments, the plasmid encodes a gene required for survival, the gene required for survival having been deleted from bacterial genome of the transformed bacterium. In yet another embodiment, the plasmid harbors a gene encoding for endosome escape, for example, pfo. In other embodiments, the foreign nucleotide sequence encodes for endosome escape, for example, for pfo. In other embodiments, the foreign nucleotide sequence codes for antigen 85a, antigen 85b, or antigen 85a/85b. In yet other embodiments, the plasmid harbors a gene encoding for proteins that maintain and/or stabilize the plasmid. In some embodiments, the gene encoding for proteins codes for antigen 85a, antigen 85b, or antigen 85a/85b. In one embodiments of the invention, the bacterium is a *Mycobacterium*. In yet another embodiment, the foreign nucleotide sequence codes for apoptosis. In other embodiments, the plasmid harbors a gene encoding for apoptosis. In yet another embodiment of the invention, the foreign nucleotide sequence cannot be replicated in Gram negative bacteria. In some embodiments, the transformed bacterium is auxotrophic. In yet another embodiments, the foreign nucleotide sequence is at least a part of a one-way shuttle vector.

The invention further provides a method of transforming a bacterium. The method comprises the step of incorporating a foreign nucleotide sequence that replicates and is expressed in the bacterium, and the foreign nucleotide sequence is not linked to a selectable marker. In one embodiment of the invention, the step of incorporation is performed by electroporation. In yet another embodiment, the foreign nucleotide sequence is on a plasmid and the electroporation is performed under the following conditions: a ratio of plasmid DNA to bacteria cells ranging from 1 µg to 5 µg of plasmid DNA to $1.25 \times 10^8$ bacterial cells. In one embodiment of the invention, the ratio is approximately 1.6 µg of plasmid to approximately $1.25 \times 10^8$ bacterial cells. In some embodiments of the invention, the foreign nucleotide sequence cannot be replicated in Gram negative bacteria. In other embodiments, the foreign nucleotide sequence is at least a part of a one-way shuttle vector. In yet further embodiments, the foreign nucleotide sequence is positioned on a plasmid and codes for a gene required for survival that is deleted from a bacterial genome of the bacterium.

The invention further provides a transformed *Mycobacterium* or progeny thereof comprising a foreign nucleotide sequence which encodes a gene of interest, and wherein one or more of the following conditions exists: a) the transformed *Mycobacterium* includes a plasmid that is incapable of replicating in Gram-negative bacteria; b) the transformed *Mycobacterium* does not exhibit antibiotic resistance; c) the transformed *Mycobacterium* is auxotrophic; and d) the transformed *Mycobacterium* harbors a one way shuttle vector. In one embodiment, the foreign nucleotide sequence is part of a plasmid. In another embodiment, the plasmid lacks a selectable marker. In yet another embodiment of the invention, the foreign nucleotide sequence codes for a gene required for survival, and wherein the gene required for survival is deleted from the bacterial genome of the transformed mycobacterium. In some embodiments, the gene required for survival is leuD. The transformed *Mycobacterium* or progeny may further comprise promoter sequences that are activated in vivo. The transformed *Mycobacterium* or progeny thereof may be attenuated. The transformed *Mycobacterium* or progeny thereof may be BCG, which may, for example, be BCG1331, BCG Pasteur, BCG Tokyo, or BCG Copenhagen.

The invention further provides a vaccine comprising a transformed *Mycobacterium* or progeny thereof comprising a foreign nucleotide sequence which encodes a gene of interest, and wherein one or more of the following conditions exist: a) the transformed *Mycobacterium* includes a plasmid which is incapable of replicating in gram-negative bacteria; b) the transformed *Mycobacterium* does not exhibit antibiotic resistance; c) the transformed *Mycobacterium* is auxotrophic; and d) the transformed *Mycobacterium* harbors a one way shuttle vector.

BRIEF DESCRIPTION OF THE DRAWINGS

FIG. 1. The map for suicide vector pAF103. The denotation for each of the DNA segments as follow: L-flank and R-flank: left and right flanks of leuD gene respectively; aph is aminoglycoside phosphotransferase gene (gene bank accession number: X06402), which confers kanamycin resistance for the plasmid; OriE is the pUC origin of replication (gene bank accession number AY234331); Ble is the gene (Genbank accession number L36850), which confers resistance to Zeocin for the plasmid; SacB is the gene (Genbank accession number: Y489048) encoding levansucrase, which confers the bacteria sensitivity to sucrose; $P_{hsp60}$ is the promoter sequence of heat shock protein gene (i.e. Rv0440); MCS is the multiple cloning sites for the indicated restriction enzymes. Note that the cassette between two PacI sites can be replaced with other endosomalytic enzyme genes when applicable.

FIG. 3. Schematic depiction of non-antibiotic expression vector for introducing expression vectors into recombinant *Mycobacterium*, i.e. rBCG. The gene to be expressed in rBCG is cloned into the plasmid via the pacI site. Before electroporation into rBCG, the plasmid is digested with the indicated restriction enzymes to remove the oriE and Kan regions, creating a one-way shuttle expression vector. The denotation for each of the DNA segments as follow: $P_{Rv3130}$ the promoter sequence of antigen Rv3130c; $P_{Ag85B}$ is the promoter sequence of antigen 85B (i.e. Rv1886c); Antigen Y is a mycobacterial antigen TB10.4 (i.e. Rv0288); Ag85B is the DNA sequence encoding antigen 85B (i.e. Rv1886c); Ag85A is the gene encoding antigen 85A (i.e. Rv3804c); aph is aminoglycoside phosphotransferase gene (gene bank accession number: X06402), which confers kanamycin resistance for the plasmid; OriE is the pUC origin of replication (Gene Bank accession number: AY234331); LeuD is the gene encoding 3-isopropylmalate dehydratase (i.e. Rv2987c); oriM is the origin of replication in *mycobacterium* (Genbank accession number: M23557).

FIG. 5. PCR analysis of selected colonies for the presence of the expression plasmid. PCR was carried as described in Materials and Methods. PCR products were analyzed by gel electrophoresis in a 1.0% agrose gel. Lane 1: A DNA ladder (Invitrogen) was used as a 1 Kb plus DNA standard. Lane 2: PCR template negative control; Lane 3: PCR for BCG strain Danish1331; Lanes 4 through 7: PCR for colonies numbered 59, 61, 69 and 84 respectively; Lane 8: a blank loading well; Lane 9: PCR for the original plasmid.

DETAILED DESCRIPTION OF THE PREFERRED EMBODIMENTS OF THE INVENTION

The present invention provides genetically engineered (recombinant) *Mycobacterium* strains with improved vaccinal properties for use as vaccinating agents against tuberculosis. They possess a variety of features, each of which serves to increase the immunogenicity of the strains. Recombinant *Mycobacterium* strains of the present invention are developed from parent strains that are purposefully selected for their potent immunogenicity. In other words, the strain of *Mycobacterium* that is selected as a parent strain to undergo genetic manipulation (for example, to overexpress a tuberculosis antigen) is chosen because, even prior to the genetic manipulation, it exhibits the ability to elicit a potent immune response in a vaccinated host. BCG strain Danish 1331 is an example. Such strains are then preferably modified, for example, to overexpress a tuberculosis antigen of interest. Preferably, a promoter that is in vivo activated is used in the genetically recombinant mycobacterium. In addition, the recombinant *Mycobacterium* strains of the present invention are genetically engineered to be selectable on a basis other than by antibiotic resistance, making them generally safe for use as vaccinating agents in human populations. As an example, a gene required for replication is removed and placed in an expression plasmid. In addition, the recombinant *Mycobacterium* strains of the present invention do not undergo horizontal transfer to gram-negative bacteria and are thus incapable of "escaping" from the host organism (i.e. they are "one-way shuttle vectors"). This also ensures their safety as vaccine agents in human populations. In addition, while the recombinant *Mycobacterium* strains of the present invention are excellent agents for use in tuberculosis vaccines, they may also be genetically engineered to express or overexpress antigens other than those relevant to tuberculosis, and are thus useful as vaccine agents against other diseases as well.

In preferred embodiments of the present invention, the *Mycobacterium* strains are attenuated strains, for example BCG. However, as will be readily recognized by those of skill in the art, other attenuated and non-attenuated *Mycobacterium* strains may also be utilized. Examples of additional types of *Mycobacteria* include but are not limited to *Mycobacterium microti, Mycobacterium* H37Ra, *Mycobacterium vaccae*, etc.

BCG Strain Selection

The prior art suggests that BCG is not a homogeneous strain but instead has developed an array of distinct genetic lineages (Oettinger et al., Tuber Lung Dis. 79(4): 243-250; 1999). Until recently it was not clear whether these differences changed the immunogenicity and potency of BCG family members. However, as described herein, it has now been discovered that the specific strain from which a recombinant BCG (herein referred to as rBCG) is derived makes a substantive difference in the immunogenic potency of rBCG. Example 1 below shows that BCG strain Danish 1331 (herein referred to as "$BCG_{1331}$") is a superior vaccine when compared to $BCG_{Tice}$. Thus, although overexpression of antigen 85B in strain rBCG30 increased the immunogenicity of parental strain $BCG_{Tice}$ from which rBCG30 was derived, rBCG30, which overexpresses antigen 85B in the BCG tice strain, did not acquire the potency of $BCG_{1331}$. Thus, certain advantages gained from antigen overexpression in BCG may be obtained by selecting a potent parent BCG strain at the initiation of the vaccine construction process. While this solution may appear obvious in hindsight, those knowledgeable in the art do not make this compensation (Horwitz et al., Proc Natl Acad Sci USA 97(25): 13853-13858; 2000), demonstrating that heretofore it was neither common nor deemed essential to first determine whether a parent BCG strain displayed an adequate potency prior to initiating the construction of rBCG vaccines. Such strains are well suited for overexpression of BCG and TB antigens or foreign antigens.

Potent parent BCG strains can be selected from the group including but not limited to $BCG_{1331}$, BCG Pasteur, BCG Tokyo and BCG Copenhagen. The parent BCG strain should reduce the level of viable *Mycobacterium tuberculosis* challenge organisms by at least $0.4\times10^{10}$ more than BCG Tice in the low-dose aerosol guinea pig challenge model as shown in Example 1 below.

Enhancing the Immunogenicity of BCG

As discussed above, the immunogenicity of BCG is not invariant. Moreover, Example 1 shows us that although the immunogenicity of BCG antigens can be enhanced through the genetic modification of BCG, such modifications are rendered moot if the parent BCG strain in which the recombinant changes were made lacks potency in the guinea pig challenge model. A corollary to this precept is that modifications that further enhance the immunogenicity of BCG will further improve the immunogenicity of recombinant strains derived from such parental strains.

Having applied the approach detailed above to select an appropriate BCG strain to serve as the parent from which rBCG vaccines and vaccine vectors are derived, genetic modifications are introduced into the strain to generate the desired rBCG vaccines and vaccine vectors. The methods employed in the construction of individual rBCG strains are not critical to the present invention and can be selected from any one or any combination of methods known by those skilled in the art (Horwitz et al., PNAS 97(25): 13853-13858; 2000; Hess et al., Proc Natl Acad Sci USA, 95: 5299-5304; 1998).

Further, the rBCG vaccines benefits from using a promoter that is activated in vivo after infection. For example, using the constitutively active promoter such as promoters from Antigen 85B, antigen 85A, Hsp60 or Rv1908c (KatG) enables the antigen to be expressed constitutively in vivo after immunization. Therefore, a robust immune response is elicited against the infection for each stage during the course of infection. While selecting the latent stage active promoters such as promoter from genes Rv2032, Rv3127, Rv2031c or Rv3030c etc enable rBCG to express the selected antigens, especially latent stage specific antigens when rBCG vaccines enter latent stage in vivo after immunization.

Expression Vectors Development of Non-Antibiotic Selection Systems As stated above, plasmids that are currently utilized for overexpression of protective antigens in rBCG strains are unacceptable due to their reliance on antibiotic resistance genes for maintenance, and an inherent ability of such plasmids to transfer horizontally to a broad array of microbial hosts, thereby posing a threat of disseminating antibiotic resistance genes and antigen expression cassettes to environmental organisms. To overcome these important limitations, the present invention describes a novel non-antibiotic selection system and a one-way shuttle system for introduction and maintenance of expression vectors in Mycobacterium host strains such as rBCG.

Non-antibiotic selection of plasmids is achieved by selectively deleting a host gene that is essential for replication and subsequently complementing the deletion by incorporating a functional copy of the gene in an expression plasmid. Thus, the bacterial hosts depend on the expression plasmid for survival, resulting in a mechanism to maintain the plasmid inside the Mycobacterium host in the absence of antibiotic selection. A preferred method entails the inactivation of genes to create an auxotrophic phenotype. For example, in M. tb and BCG, inactivation of the leuD gene (Genome Seq ID# Mb3011C) creates a leucine-dependent phenotype and strains that possess an inactivated leuD gene are dependent on leucine supplementation to survive (Hondalus et al., Infect Immun. 68(5): 2888-98. 2000). In addition, Mycobacterium ΔleuD strains are incapable of replication in vivo (Hondalus et al., supra, 2000), thus M. tb and rBCG ΔleuD mutants will maintain leuD$^+$ plasmids in vitro and in vivo.

The specific method for introducing the auxotrophic mutation into target Mycobacterium strains is not important to the present invention and may be selected from any allelic exchange methods well known to those skilled in the art (Parish et al., Microbiology, 145: 3497-3503; 1999). Similarly, complementation of the auxotrophic mutation is achieved by introducing a functional copy of the inactivated gene (e.g. leuD$^+$) onto the expression vector. The expression vector also requires a Mycobacterium origin of replication (e.g. OriM; Labidi et al., Plasmid, 27(2): 130-140; 1992) to enable replication in target M. tb and rBCG strains. Mycobacterium strains harboring such a plasmid will be dependent on the expression of plasmid-encoded leuD gene for survival upon withdrawal of leucine from the media.

Development of Novel One-Way Shuttle Vectors

The above procedure describes an approach to create a selection system for maintenance of expression vectors in M. tb and rBCG. However, this vector system must be capable of replication in Escherichia coli to enable efficient manipulation of the plasmid structure prior to introduction into Mycobacterium. Furthermore, to broaden potential recombinant E. coli host strains that can be utilized during plasmid construction, thereby allowing researchers to use an E. coli host that facilitates plasmid construction, it is preferable to include an antibiotic selection marker (e.g. kanamycin-resistance) and a broad host range origin of replication (e.g. OriE; Halpern et al., Proc Natl Acad Sci, USA 76(12): 6137-6141; 1979; Mosig et al., New Biol 1(2): 171-179; 1989) in the expression vector. These elements are flanked by unique restriction endonuclease digestion sites (e.g. NdeI) to enable removal of the antibiotic resistance marker and the E. coli origin of replication before introducing the plasmid into target Mycobacterium strains. In addition, unique restriction endonuclease sites (e.g. PacI) into which antigen expression cassettes may be introduced are included.

Once this has been accomplished in E. coli and the desired plasmid has been identified and characterized, recombinant plasmid DNA is isolated and digested with the restriction endonuclease that liberates the antibiotic selection marker and the OriE. The digested plasmid DNA is then ligated using T4 DNA ligase. The resulting plasmid thus contains the gene that complements the auxotrophy of the host Mycobacterium, but does not exhibit antibiotic resistance, and is not capable of replicating in gram-negative bacteria. The plasmid, which may also include an antigen expression cassette, is then introduced into the target Mycobacterium auxotrophic mutant using standard electroporation procedures. Recombinant strains harboring the plasmid are isolated by culturing in media that lacks the metabolite that is required for growth (e.g. leucine). The unique advantage of this system is that the final expression plasmid no longer possesses the antibiotic resistance gene. Thus it cannot spread the antibiotic resistance gene to the environment like current commonly used expression plasmids. In addition, the expression plasmid of the present invention is no longer capable of replication in a broad host range, since the genetic elements that enable such replication are deleted. Such vectors are thus denominated "one-way" shuttle vectors.

Overexpression of TB Antigens

In the present invention, the gene incorporated in the expression cassette in the one-way shuttle vector and then into the rBCG may encode a M. tb immunogen. The M. tb immunogen may be, for example, a full-length native protein, a chimeric fusion between two or more M. tb immunogens or mimetics, or a fragment or fragments of a M. tb immunogen that originates from Mycobacterium tuberculosis.

M. tb antigens are expressed by the one-way shuttle vector under the control of a promoter that is active during at least one stage of mycobacterial infection in vivo. The particular promoter is not important to the present invention but may be selected from promoters that are constitutively active such as: Antigen 85B, Hsp60, Antigen 85A, Rv1908c (KatG), and/or promoters that are active during latent infection such as the promoter for genes Rv3130C (Florozyk et al., Infect Immun 71(9): 5332-5343; 2003; Voskuil et al., J Exr Med 198(5): 705-713; 2003), Rv2032, Rv3127, and/or Rv2031c. To increase the level of antigen expression, a mini-cell producing derivative of the Mycobacterium vector strains may be used. Mini-cell producing strains of Mycobacterium species are produced by over-expressing FtsZ (Genome database # Mb2174c) or by site-directed inactivation of whiB3. Modification of the FtsZ expression level or inactivation of whiB3 can be accomplished using standard genetic methods well known to those skilled in the art. For example, FtsZ overexpression is accomplished by incorporating the ftsZ gene into the one-way shuttle vector under the control of a strong promoter, such as promoters for Antigen 85B, Antigen 85A, Hsp60, or Rv1908c (KatG), which are constitutively active, and/or promoters that are active during latent infection such as promoters for genes Rv2032, Rv3127, Rv2031c, and Rv3130C (Florczyk et al., supra; 2003; Voskuil et al., supra, 2003). Site-directed inactivation of whiB3 is accomplished by allelic exchange using the procedures outlined below.

Examples of Foreign Antigens that can be Inserted in Recombinant Mycobacterium

In the present invention, the expression cassette in the one-way shuttle vector carried by the Mycobacterium vector may encode an immunogen, which may be either a foreign immunogen from viral, bacterial or parasitic pathogens, or an endogenous immunogen, such as but not limited to an autoimmune antigen or a tumor antigen. The immunogens may be, for example, a full-length native protein; chimeric fusions between a foreign immunogen and an endogenous protein or mimetic; or a fragment or fragments of an immunogen that originates from viral, bacterial and parasitic pathogens.

As used herein, "foreign immunogen" means a protein or fragment thereof, which is not normally expressed in the recipient animal cell or tissue, such as, but not limited to, viral proteins, bacterial proteins, parasite proteins, cytokines, chemokines, immunoregulatory agents, or therapeutic agents.

An "endogenous immunogen" means a protein or part thereof that is naturally present in the recipient animal cell or tissue, such as, but not limited to, an endogenous cellular protein, an immunoregulatory agent, or a therapeutic agent. Alternatively or additionally, the immunogen may be encoded by a synthetic gene and may be constructed using conventional recombinant DNA methods known to those of skill in the art.

The foreign immunogen can be any molecule that is expressed by any viral, bacterial, or parasitic pathogen prior to or during entry into, colonization of, or replication in its animal host. The rBCG may express immunogens or parts thereof that originate from viral, bacterial and parasitic pathogens. These pathogens can be infectious in humans, domestic animals or wild animal hosts.

The viral pathogens, from which the viral antigens are derived, include, but are not limited to, orthomyxoviruses, such as influenza virus (Taxonomy ID: 59771; retroviruses, such as RSV, HTLV-1 (Taxonomy ID: 39015), and HTLV-II (Taxonomy ID: 11909); Herpes viruses such as EBV Taxonomy ID: 10295); CMV (Taxonomy ID: 10358) or herpes simplex virus (ATCC #: VR-1487); lentiviruses, such as HIV-1 (Taxonomy ID: 12721) and HIV-2 Taxonomy ID: 11709); rhabdoviruses, such as rabies; picornoviruses, such as Poliovirus (Taxonomy ID: 12080); poxviruses, such as vaccinia (Taxonomy ID: 10245); Rotavirus (Taxonomy ID: 10912); and parvoviruses, such as adeno-associated virus 1 (Taxonomy ID: 85106).

Examples of viral antigens can be found in the group including but not limited to the human immunodeficiency virus antigens Nef (National Institute of Allergy and Infectious Disease HIV Repository Cat. # 183; Genbank accession # AF238278), Gag, Env (National Institute of Allergy and Infectious Disease HIV Repository Cat. # 2433; Genbank accession # U39362), Tat (National Institute of Allergy and Infectious Disease HIV Repository Cat. # 827; Genbank accession # M13137), mutant derivatives of Tat, such as Tat-Δ31-45 (Agwale et al. Proc. Natl. Acad. Sci. Jul. 23, 2002 99(15): 10037-10042), Rev (National Institute of Allergy and Infectious Disease HIV Repository Cat. # 2088; Genbank accession # L14572), and Pol (National Institute of Allergy and Infectious Disease HIV Repository Cat. # 238; Genbank accession # AJ237568) and T and B cell epitopes of gp 120 (Hanke and McMichael, AIDS Immunol Lett., 66:177; 1999; Hanke, et al., Vaccine, 17:589; 1999; Palker et al, J. Immunol., 142:3612 3619; 1989), chimeric derivatives of HIV-1Env and gp 120, such as but not restricted to fusion between gp 120 and CD4 (Fouts et al., J. Virol. 2000, 74:11427-11436; 2000); truncated or modified derivatives of HIV-1 env, such as but not restricted to gp 140 (Stamatos et al. J Virol, 72:9656-9667; 1998), or derivatives of HIV-1 Env and/or gp 140 thereof (Binley, et al. J Virol, 76:2606-2616; 2002; Sanders, et al. J Virol, 74:5091-5100; 2000; Binley, et al. J Virol, 74:627-643; 2000), the hepatitis B surface antigen (Genbank accession # AF043578; Wu et al., Proc. Natl. Acad. Sci., USA, 86:4726 4730; 1989); rotavirus antigens, such as VP4 (Genbank accession # AJ293721; Mackow et al., Proc. Natl. Acad. Sci., USA, 87:518 522; 1990) and VP7 (GenBank accession # AY003871; Green et al., J. Virol., 62:1819 1823; 1988), influenza virus antigens such as hemagglutinin (GenBank accession # AJ404627; Pertmer and Robinson, Virology, 257:406; 1999); nucleoprotein (GenBank accession # AJ289872; Lin et al, Proc. Natl. Acad. Sci., 97: 9654-9658; 2000) herpes simplex virus antigens such as thymidine kinase (Genbank accession # AB047378; Whitley et al, In: New Generation Vaccines, pages 825-854; 2004).

The bacterial pathogens, from which the bacterial antigens are derived, include but are not limited to, *Mycobacterium* spp., *Helicobacter pylori*, *Salmonella* spp., *Shigella* spp., *E. coli*, *Rickettsia* spp., *Listeria* spp., *Legionella pneumoniae*, *Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen (Yamamoto et al., Infect. Immun., 50:925-928; 1985) and the nontoxic B-subunit of the heat-labile toxin (Klipstein et al., Infect. Immun., 40:888-893; 1983); pertactin of *Bordetella pertussis* (Roberts et al., Vacc., 10:43-48; 1992), adenylate cyclase-hemolysin of *B. pertussis* (Guiso et al., Micro. Path., 11:423-431; 1991), fragment C of tetanus toxin of *Clostridium tetani* (Fairweather et al., Infect. Immun., 58:1323-1326; 1990), OspA of *Borellia burgdorferi* (Sikand, et al., Pediatrics, 108:123-128; 2001); Wallich, et al., Infect Immun, 69:2130-2136; 2001), protective paracrystalline-surface-layer proteins of *Rickettsia prowazekii* and *Rickettsia typhi* (Carl, et al., Proc Natl Acad Sci USA, 87:8237-8241; 1990), the listeriolysin (also known as "Llo" and "Hly") and/or the superoxide dismutase (also known as "SOD" and "p60") of *Listeria monocytogenes* (Hess, J., et al., Infect. Immun. 65:1286-92; 1997; Hess, J., et al., Proc. Natl. Acad. Sci. 93:1458-1463; 1996; Bouwer, et al., J. Exp. Med. 175:1467-71; 1992), the urease of *Helicobacter pylori* (Gomez-Duarte, et al., Vaccine 16, 460-71; 1998; Corthesy-Theulaz, et al., Infection & Immunity 66, 581-6; 1998), and the receptor-binding domain of lethal toxin and/or the protective antigen of *Bacillus anthrax* (Price, et al., Infect. Immun. 69, 4509-4515; 2001).

The parasitic pathogens, from which the parasitic antigens are derived, include but are not limited to: *Plasmodium* spp. such as *Plasmodium falciparum* (ATCC# 30145); *Trypanosome* spp. such as *Trypanosoma cruzi* (ATCC# 50797); *Giardia* spp. such as *Giardia intestinalis* (ATCC# 30888D); *Boophilus* spp., *Babesia* spp. such as *Babesia microti* (ATCC# 30221); *Entamoeba* spp. such as *Entamoeba histolytica* (ATCC# 30015); *Eimeria* spp. such as *Eimeria maxima* (ATCC# 40357); *Leishmania* spp. (Taxonomy ID: 38568); *Schistosome* spp., *Brugia* spp., *Fascida* spp., *Dirofilaria* spp., *Wuchereria* spp., and *Onchocerea* spp.

Examples of protective antigens of parasitic pathogens include the circumsporozoite antigens of *Plasmodium* spp. (Sadoff et al., Science, 240:336-337; 1988), such as the circumsporozoite antigen of *P. bergerii* or the circumsporozoite antigen of *P. falciparum*; the merozoite surface antigen of *Plasmodium* spp. (Spetzler et al., Int. J. Pept. Prot. Res., 43:351-358; 1994); the galactose specific lectin of *Entamoeba histolytica* (Mann et al., Proc. Natl. Acad. Sci., USA, 88:3248-3252; 1991), gp63 of *Leishmania* spp. (Russell et al., J. Immunol., 140:1274-1278; 1988; Xu and Liew, Immunol., 84: 173-176; 1995), gp46 of *Leishmania major* (Handman et al., Vaccine, 18: 3011-3017; 2000), paramyosin of *Brugia malayi* (Li et al., Mol. Biochem. Parasitol., 49:315-323; 1991), the triose-phosphate isomerase of *Schistosoma mansoni* (Shoemaker et al., Proc. Natl. Acad. Sci., USA, 89:1842-1846; 1992); the secreted globin-like protein of *Tri-* chostrongylus colubriformis (Frenkel et al., Mol. Biochem. Parasitol., 50:27-36; 1992); the glutathione-S-transferase's of *Frasciola hepatica* (Hillyer et al., Exp. Parasitol., 75:176-186; 1992), *Schistosoma bovis* and *S. japonicum* (Bashir et al., Trop. Geog. Med., 46:255-258; 1994); and KLH of *Schistosoma bovis* and *S. japonicum* (Bashir et al., supra 1994).

As mentioned earlier, the rBCG vaccines may encode an endogenous immunogen, which may be any cellular protein, immunoregulatory agent, or therapeutic agent, or parts thereof, that may be expressed in the recipient cell, including but not limited to tumor, transplantation, and autoimmune immunogens, or fragments and derivatives of tumor, transplantation, and autoimmune immunogens thereof. Thus, in the present invention, rBCGs may encode tumor, transplant, or autoimmune immunogens, or parts or derivatives thereof. Alternatively, the rBCG may encode synthetic genes (as described above), which encode tumor-specific, transplant, or autoimmune antigens or parts thereof.

Examples of tumor specific antigens include prostate specific antigen (Gattuso et al., Human Pathol., 26:123-126; 1995), TAG-72 and CEA (Guadagni et al., Int. J. Biol. Markers, 9:53-60; 1994), MAGE-1 and tyrosinase (Coulie et al., J. Immunothera., 14:104-109; 1993). Recently it has been shown in mice that immunization with non-malignant cells expressing a tumor antigen provides a vaccine effect, and also helps the animal mount an immune response to clear malignant tumor cells displaying the same antigen (Koeppen et al., Anal. N.Y. Acad. Sci., 690:244-255; 1993).

Examples of transplant antigens include the CD3 molecule on T cells (Alegre et al., Digest. Dis. Sci., 40:58-64; 1995). Treatment with an antibody to CD3 receptor has been shown to rapidly clear circulating T cells and reverse cell-mediated transplant rejection (Alegre et al., supra, 1995).

Examples of autoimmune antigens include IAS β chain (Topham et al., Proc. Natl. Acad. Sci., USA, 91:8005-8009; 1994). Vaccination of mice with an 18 amino acid peptide from IAS β chain has been demonstrated to provide protection and treatment to mice with experimental autoimmune encephalomyelitis (Topham et al., supra, 1994).

Development of rBCG that Express an Adjuvant rBCG can be constructed that encode an immunogen and an adjuvant, and can be used to increase host responses to the rBCG. Alternatively, rBCG can be constructed that encode an adjuvant, in mixtures with other rBCG to increase host responses to immunogens encoded by the partner rBCG.

The particular adjuvant encoded by the rBCG is not critical to the present invention and may be the A subunit of cholera toxin (i.e. CtxA; GenBank accession no. X00171, AF175708, D30053, D30052), or parts and/or mutant derivatives thereof (e.g. the A1 domain of the A subunit of Ctx (i.e. CtxA1; GenBank accession no. K02679), from any classical *Vibrio cholerae* (e.g. *V. cholerae* strain 395, ATCC # 39541) or E1 Tor *V. cholerae* (e.g. *V. cholerae* strain 2125, ATCC # 39050) strain. Alternatively, any bacterial toxin that is a member of the family of bacterial adenosine diphosphate-ribosylating exotoxins (Krueger and Barbier, Clin. Microbiol. Rev., 8:34; 1995), may be used in place of CtxA, for example the A subunit of heat-labile toxin (referred to herein as E1tA) of enterotoxigenic *Escherichia coli* (GenBank accession # M35581), pertussis toxin S1 subunit (e.g. ptxS1, GenBank accession # AJ007364, AJ007363, AJ006159, AJ006157, etc.); as a further alternative the adjuvant may be one of the adenylate cyclase-hemolysins of *Bordetella pertussis* (ATCC # 8467), *Bordetella bronchiseptica* (ATCC # 7773) or *Bordetella parapertussis* (ATCC # 15237), e.g. the cyaA genes of *B. pertussis* (GenBank accession no. X14199), *B. parapertussis* (GenBank accession no. AJ249835) or *B. bronchiseptica* (GenBank accession no. Z37112).

Development of rBCG that Express an Immunoregulatory Agent rBCG can be constructed that encode an immunogen and a cytokine, and can be used to increase host responses to the rBCG. Alternatively, rBCG can be constructed that encode said cytokine alone, in mixtures with other rBCG to increase host responses to immunogens encoded by the partner rBCG.

The particular cytokine encoded by the rBCG is not critical to the present invention and may include, but is not limited to, interleukin-4 (herein referred to as "IL-4"; Genbank accession no. AF352783 (Murine IL-4) or NM_000589 (Human IL-4)), IL-5 (Genbank accession no. NM_010558 (Murine IL-5) or NM_000879 (Human IL-5)), IL-6 (Genbank accession no. M20572 (Murine IL-6) or M29150 (Human IL-6)), IL-10 (Genbank accession no. NM_010548 (Murine IL-10) or AF418271 (Human IL-10)), Il-12$_{p40}$ (Genbank accession no. NM_008352 (Murine IL-12 p40) or AY008847 (Human IL-12 p40)), IL-12$_{p70}$ (Genbank accession no. NM_008351/ NM_008352 (Murine IL-12 p35/40) or AF093065/ AY008847 (Human IL-12 p35/40)), TGFβ (Genbank accession no. NM_011577 (Murine TGFβ1) or M60316 (Human TGFβ1)), and TNFα Genbank accession no. X02611 (Murine TNFα) or M26331 (Human TNFα)).

Apoptosis is programmed cell death, which differs dramatically from necrotic cell death in terms of its induction and consequences. Apoptosis of cells containing foreign antigens is a powerful known stimulus of cellular immunity against such antigens. The process by which apoptosis of antigen containing cells leads to cellular immunity has sometimes been called cross-priming. (Heath, W. R., G. T. Belz, G. M. Behrens, C. M. Smith, S. P. Forehan, I. A., Parish, G. M. Davey, N. S. Wilson, F. R. Carbone, and J. A. Villandangos. 2004. Cross-presentaion, dentritic cell subsets, and the generation of immunity to cellular antigens. *Immunol Rev* 199:9; Gallucci, S., M. Lolkema, and P. Matzinger. 1999. Natural adjuvants:Endogenous activators of dendritic cells. *Nature Biotechnology.* 5:1249; Albert, M. L., B. Sauter, and N. Bhadrdwaj. 1998. Dendtritic cells acquire antigen from apoptotic cells and induce class I-restricted CTLs. *Nature* 392: 86). There are several mechanisms for induction of apoptosis which lead to increased antigen specific cell mediated immunity. Caspase 8 mediated apoptosis leads to antigen specific cellular immune protection. Production of Caspase 8 by rBCG and secretion in the eukaryotic cell cytoplasm by rBCG in the context of foreign antigens expressed by the rBCG, against BCG and other tuberculosis antigens over-expressed by the rBCG as well as against antigens of BCG itself will lead to high levels of antigen specific cellular immunity. Death receptor-5 (DR-5) also known as TRAIL-R2 (TRAIL receptor 2) or TNFR-SF-10B (Tumor Necrosis Factor-Superfamily member 10B) also mediates caspase 8 mediated apoptosis (Sheridan, J. P., S. A. Marsters, R. M. Pitti, A. Gruney, M. Skutbatch, D. Baldwin, L. Ramakrishnan, C. L. Gray, K. Baker, W. I. Wood, A. D. Goddard, P. Godowski, and A. Ashkenazi. 1997. Control of Trail induced apoptosis by a family of signaling and decoy receptors. *Science* 277:818). Reovirus induced apoptosis is mediated by TRAIL-DR5 leading to subsequent clearance of the virus (Clarke, P., S. M. Meintzer, S. Gibson, C. Widmann, T. P. Garrington, G. L. Johnson, and K. L. Tyler. 2000. Reovirus-induced apoptosis is mediated by TRAIL. *J Virol* 74:8135). Expression of DR-5 by recombinant BCG will provide a potent adjuvant effect for induction of antigen specific cellular immunity against rBCG expressed antigens. Antigen expressing cells can also be induced to undergo apoptosis through Fas ligation which is a strong stimulus for induction of antigen specific cellular immune responses (Chattergoon, M. A., J. J. Kim, J. S. Yang, T. M. Robbinson, D. J. Lee, T. Dentchev, D. M. Wilson, V. Ayyavoo, and D. B. Weiner. 2000. Targeted antigen delivery to antigen-presenting cells including dendritic cells by engineered Fas-mediated apoptosis. *Nat Biotechnology* 18:974). Recombinant BCG expressing Fas or Fas cytoplasmic domain/CD4 ectodomain fusion protein will induce apoptosis and antigen specific cellular immune responses.

The enhancement of cellular immunity by rBCG, which produce enhancers of apoptosis as described above is not limited to BCG antigens or antigens specifically coded for over-expression by rBCG but includes any antigen in the eukaryotic cell the aforementioned rBCG can invade. As an example if such an rBCG is delivered to tumor cells where apoptosis is induced then cellular immunity against important tumor antigens will be induced with elimination, reduction or prevention of the tumor and/or metastasis. This anti-tumor effect will be in addition to the general anti-tumor effect that BCG generates when given locally such as the case with bladder cancer.

In a further embodiment of this invention, rBCG enhanced by production of specific mediators of apoptosis, delivered inside tumor or other cells wherein such rBCG also produce foreign antigens against which strong cellular immune responses will be mounted will induce the production of strong cellular responses against those cells containing these foreign antigens. These cellular responses will lead to immune mediated tumor cell destruction, further cross priming and induction of cellular immunity against tumor or other important antigens with subsequent elimination, reduction or prevention of the tumor and/or metastasis. An example of such a foreign antigen is an HLA antigen different from the host cell HLA against which a strong heterologous cellular response will be mounted.

rBCG whose apoptotic induction properties are enhanced by expression of specific mediators of apoptosis that also express specific tumor antigens will induce strong antigen specific cellular responses against these tumor antigens, including breaking of some tolerance for these antigens leading to elimination, reduction or prevention of tumors and/or metastasis without the need for direct delivery of the rBCG into the tumor itself.

Apoptosis following DNA damage or caspase 9 induces tolerance to certain antigens (Hugues, S., E. Mougneau, W. Ferlin, D. Jeske, P. Hofman, D. Homann, L. Beaudoin, D. Schrike, M. Von Herrath, A. Lehuen, and N. Glaichenenhaus. 2002). Tolerance to islet antigens and prevention from diabetes induced by limited apoptosis of pancreatic beta cells. *Immunity* 16:169). Induction of tolerance is important in controlling or preventing autoimmune diseases such as but not limited to diabetes, rheumatoid arthritis, Crohns disease, imflammatory bowel disease and multiple sclerosis. Production of caspase 9 or other apoptosis mediated tolerance inducing proteins by rBCG in cells such as but not limited to B pancreatic cells, colorectal and nerve cells will produce limited apoptosis which will induce tolerance against the antigen targets of autoimmunity in those cells thereby treating or preventing the autoimmune disease condition. Identification of specific antigens involved in autoimmune reactions will allow induction of tolerance against these autoimmune target antigens through rBCG production of both these antigens and caspase 9 or other molecules capable of inducing apoptotic mediated tolerance. Such rBCG will treat and/or prevent these autoimmune diseases.

Recombinant DNA and RNA procedures for the introduction of functional expression cassettes to generate rBCG capable of expressing an immunoregulatory agent in eukaryotic cells or tissues are described below.

The following examples are to be considered as exemplary of various aspects of the present invention and are no intended to be limiting with respect to the practice of the invention. Those of ordinary skill in the art will appreciate that alternative materials, conditions, and procedures may be varied and remain within the skill of the ordinarily skilled artisan without departing from the general scope of the invention as taught in the specification.

EXAMPLES

Methods

Cultivation of *Mycobacterium* Strains

Selected BCG strains are cultured in liquid media, such as Middlebrook 7H9 or Saulton Synthetic Medium, preferably at 37° C. The strains can be maintained as static or agitated cultures. In addition the growth rate of BCG can be enhanced by the addition of oleic acid (0.06% v/v; Research Diagnostics Cat. No. 01257) and detergents such as Tyloxapol (0.05% v/v; Research Diagnostics Cat. No.70400). The purity of BCG cultures can be evaluated by evenly spreading 100 mcl aliquots of the BCG culture serially diluted (e.g. 10-fold steps from Neat -10-8) in phosphate buffered saline (herein referred to PBS) onto 3.5 inch plates containing 25-30 ml of solid media, such as Middlebrook 7H10. In addition, the purity of the culture can be further assessed using commercially available kits such as thioglycolate medium (Science Lab, catalogue #1891) and soybean-casin medium (BD, catalogue # 211768).

BCG seed lots are stored at −80° C. at a density of $0.1-2\times10^7$ cfu/ml. The liquid cultures are typically harvested at an optical density (at 600 mm) of 0.2-4.0 relative to a sterile control; the cultures are placed into centrifuge tubes of an appropriate size and the organisms are subjected to centrifugation at 8,000×g for 5-10 min. The supernatant is discarded and the organisms are resuspended in storage solution comprised of Middlebrook 7H9 containing 10-30% (v/v) glycerol at a density of $0.1-2\times10^7$ cfu/ml. These suspensions are dispensed into sterile 1.5 ml boron silicate freezer vials in 1 ml aliquots and then placed at −80° C.

General Molecular Biology Techniques

Restriction endonucleases (herein "REs"); New England Biolabs Beverly, Mass.), T4 DNA ligase (New England Biolabs, Beverly, Mass.) and Taq polymerase (Life Technologies, Gaithersburg, Md.) are used according to the manufacturers' protocols; Plasmid DNA is prepared using small-scale (Qiagen Miniprep$^R$ kit, Santa Clarita, Calif.) or large-scale (Qiagen Maxiprep$^R$ kit, Santa Clarita, Calif.) plasmids DNA purification kits according to the manufacturer's protocols (Qiagen, Santa Clarita, Calif.); Nuclease-free, molecular biology grade milli-Q water, Tris-HCl (pH 7.5), EDTA pH 8.0, 1M MgCl$_2$, 100% (v/v) ethanol, ultra-pure agarose, and agarose gel electrophoresis buffer are purchased from Life Technologies, Gaithersburg, Md. RE digestions, PCRs, DNA ligation reactions and agarose gel electrophoresis are conducted according to well-known procedures (Sambrook, et al., Molecular Cloning: A Laboratory Manual. 1, 2, 3; 1989); Straus, et al., Proc Natl Acad Sci USA. March; 87(5) 1889-93; 1990). Nucleotide sequencing to verify the DNA sequence of each recombinant plasmid described in the following sections was accomplished by conventional automated DNA sequencing techniques using an Applied Biosystems automated sequencer, model 373A.

PCR primers are purchased from commercial vendors such as Sigma (St. Louis, Mo.) and are synthesized using an Applied Biosystems DNA synthesizer (model 373A). PCR primers are used at a concentration of 150-250 µM and annealing temperatures for the PCR reactions are determined using Clone manager software version 4.1 (Scientific and Educational Software Inc., Durham N.C.). PCRs are conducted in a Strategene Robocycler, model 400880 (Strategene, La Jolla, Calif.). The PCR primers for the amplifications are designed using Clone Manager® software version 4.1 (Scientific and Educational Software Inc., Durham N.C.). This software enabled the design PCR primers and identifies RE sites that are compatible with the specific DNA fragments being manipulated. PCRs are conducted in a thermocycler device, such as the Strategene Robocycler, model 400880 (Strategene), and primer annealing, elongation and denaturation times in the PCRs are set according to standard procedures (Straus et al., supra, 1990). The RE digestions and the PCRs are subsequently analyzed by agarose gel electrophoresis using standard procedures (Straus et al., supra, 1990; and Sambrook et al., supra, 1989). A positive clone is defined as one that displays the appropriate RE pattern and/or PCR pattern. Plasmids identified through this procedure can be further evaluated using standard DNA sequencing procedures, as described above.

*Escherichia coli* strains, such as DH5α and Sable2$^R$, are purchased from Life Technologies (Gaithersburg, Md.) and serve as initial host of the recombinant plasmids described in the examples below. Recombinant plasmids are introduced into *E. coli* strains by electroporation using a high-voltage electropulse device, such as the Gene Pulser (BioRad Laboratories, Hercules, Calif.), set at 100-200 Ω, 15-25 µF and 1.0-2.5 kV, as described (Straus et al., supra, 1990). Optimal electroporation conditions are identified by determining settings that result in maximum transformation rates per mcg DNA per bacterium.

Bacterial strains are grown on tryptic soy agar (Difco, Detroit, Mich.) or in tryptic soy broth (Difco, Detroit, Mich.), which are made according to the manufacturer's directions. Unless stated otherwise, all bacteria are grown at 37° C. in 5% $CO_2$ (v/v) with gentle agitation. When appropriate, the media are supplemented with antibiotics (Sigma, St. Louis, Mo.). Bacterial strains are stored at −80° C. suspended in (Difco) containing 30% (v/v) glycerol (Sigma, St. Louis, Mo.) at ca. $10^9$ colony-forming units (herein referred to as "cfu") per ml.

Allelic Exchange in BCG

The prior art teaches methods for introducing altered alleles into *Mycobacterium* strains and those skilled in the art will be capable of interpreting and executing such methods (Parish et al., Microbiology 146: 1969-1975; 2000). A novel method to generate an allelic exchange plasmid entails the use of synthetic DNA. The advantage of this approach is that the plasmid product will have a highly defined history and will be compliant with governmental regulations, whereas previously used methods, although effective, have poorly documented laboratory culture records and thus are unlikely to be compliant. Compliance with said regulation is essential if a product is to be licensed for use in humans by United States and European regulatory authorities.

Figure 1:
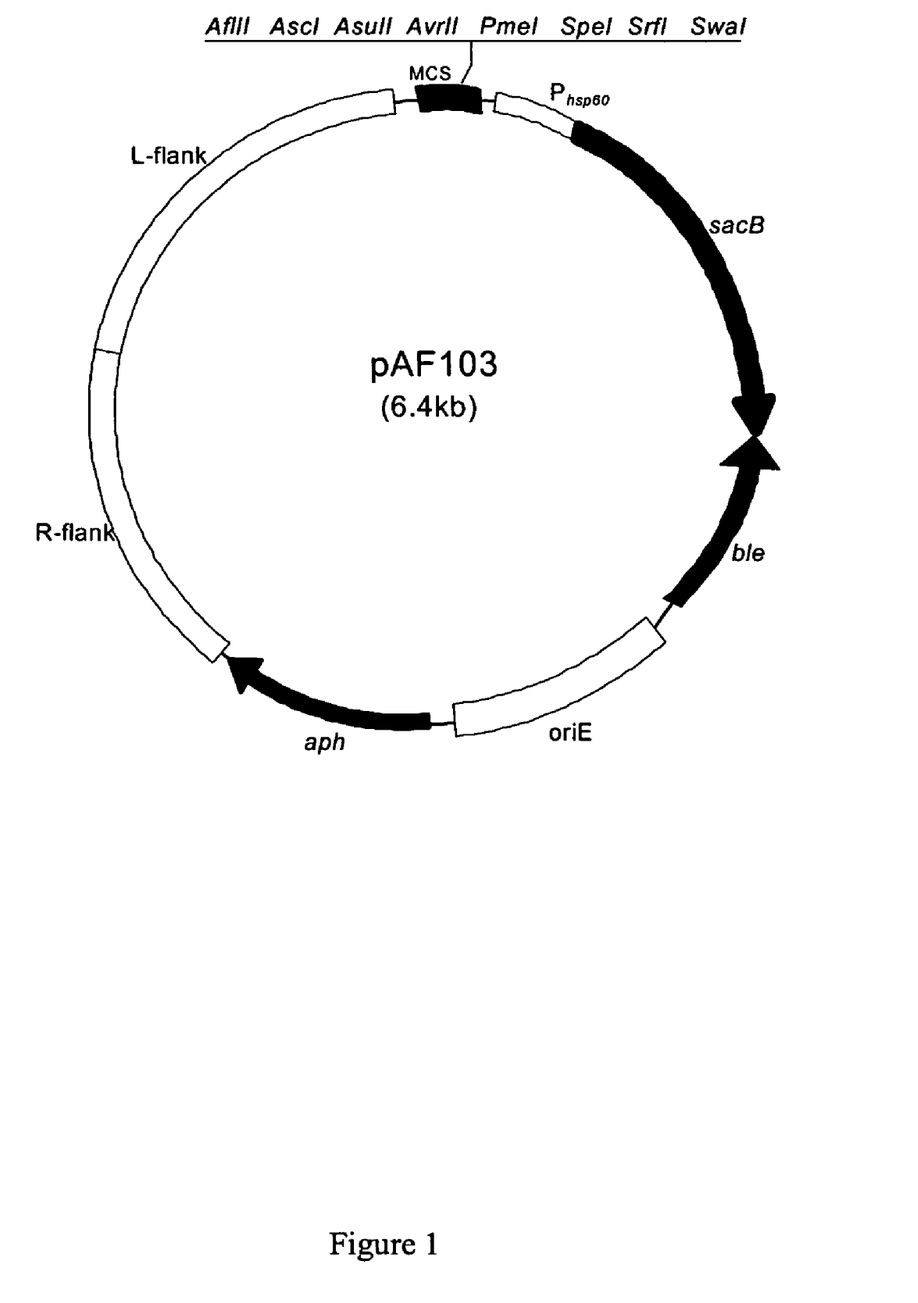

A suicide vector for allelic exchange in *Mycobacterium* is a plasmid that has the ability to replicate in *E. coli* strains but is incapable of replication in *Mycobacterium* spp., such as M. tb and BCG. The specific suicide vector for use in allelic exchange procedures in the current invention is not important and can be selected from those available from academic (Parish et al., supra, 2000) and commercial sources. A preferred design of a suicide plasmid for allelic exchange is shown in FIG. 1. The plasmid is comprised of the following DNA segments: an oriE sequence for the plasmid to replicate in *E. coli* (GenBank accession # L09137), a kanamycin-resistance sequence for selection in both *E. coli* and *Mycobacterium* (GenBank accession # AAM97345), and an additional antibiotic selection marker (e.g. the zeocin-resistance gene (GenBank accession # AAU06610), which will be under the control of a *Mycobacterium* promoter (e.g. the hsp60 promoter). The second antibiotic selection marker is not essential but is included to enable double selection to prevent outgrowth of spontaneous kanamycin-resistant isolates during the allelic exchange process (Garbe et al., Microbiology 140: 133-138; 1994).

Construction of such suicide vectors can be accomplished using standard recombinant DNA techniques as described herein. However, current regulatory standards have raised the specter of introducing prion particles acquired from products exposed bovine products containing BSE-infected material. To avoid introducing materials (e.g. DNA sequences) into the target strain of unknown origin, therefore, it is preferable that all DNA in the suicide vector are made synthetically by commercial sources (e.g. Picoscript, Inc.). Accordingly, a preferred method for constructing suicide vectors is to assemble a plan of the DNA sequences using DNA software (e.g. Clone Manager), then to synthesize the DNA on a fee-for-service basis by any commercial supplier that offer such a service (e.g. Picoscript Inc.). This method was used to produce a suicide vector, pAF100 (not shown) that was then further modified for the present particular application (pAF103, depicted schematically in FIG. 1 and described further in Table 1).

TABLE 1

Suicide vector

| Name | Backbone | Specific allele for allele exchange |
|---|---|---|
| pAF103 | pAF100 | 1 kb flanking regions of leuD gene |

Such a suicide vector has advantages, such as containing two antibiotic selection markers, thus minimizing selection of spontaneous mutants that display resistance to one antibiotic, which occurs at ca. $1/10^8$ per generation. Spontaneous resistance to two antibiotics is extremely rare and only occurs at ca. $1/10^{16}$ per generation. Thus, there is less that $1/10^6$ probability of double resistant strains emerging in the cultures used to execute the allelic exchange procedure.

For negative selection during allelic exchange process, a sacB gene (Genome Seq ID # NT01BS4354), which imparts a sucrose-sensitive phenotype, is included to enrich cultures with strains that have undergone the final DNA recombination step and completed the allelic exchange.

Formulation and Vaccination Strategies

The strategy for vaccine formulation is structured on studies to determine maximum viability and stability throughout the manufacturing process. This includes determination of maximum organism viability (live to dead) during culture utilizing a variety of commonly used medium for the culture of *Mycobacteria* to include the addition of glycerol, sugars, amino acids, and detergents or salts. After culture cells are harvested by centrifugation or tangential flow filtration and resuspended in a stabilizing medium that allows for protection of cells during freezing or freeze-drying process. Commonly used stabilizing agents include sodium glutamate, or amino acid or amino acid derivatives, glycerol, sugars or commonly used salts. The final formulation will provide sufficient viable organism to be delivered by intradermal, percutaneous injection, perfusion or oral delivery with sufficient stability to maintain and adequate shelf life for distribution and use.

Preclinical Evaluation of TB Vaccines

General Safety Test

BALB/c mice in groups of six are infected intraperitoneally with $2\times10^6$ CFU of the rBCG strain(s) of interest and the analogous parental strains. The animals are monitored for general health and body weight for 14 days post infection. Animals that receive the BCG and rBCG strains remain healthy, and neither lose weight nor display overt signs of disease during the observation period.

Virulence of Novel rBCG Strains in Immunocompetent Mice

Groups of 15 immunocompetent BALB/c mice are infected intravenously with $2\times10^6$ rBCG and BCG parental strain respectively. At day one post infection, three mice in each group will be sacrificed and CFU in spleen, lung and live are analyzed to ensure each animal has equal infection dose. At week 4, 8, 12, and 16 post infection, three mice in each group are sacrificed and CFU in spleen, liver and lung are obtained to assess the in vivo growth of the rBCG strains as compared to the parental BCG strain. rBCG strains are expected to display similar virulence to that of the parental BCG.

Stringent Safety Test in Immunocompromised Mice

Immunocompromised mice possessing the SCID (severe combined immunodeficiency) in groups of 10 are infected intravenously with $2\times10^6$ cfu rBCG and the parental BCG strain respectively. At day one after infection, three mice in each group are sacrificed and cfu in spleen, liver and lung is assessed to verify the inoculation doses. The remaining seven mice in each group are monitored for general health and body weight. The survival of these mice is followed and successful results are when the survival of rBCG-infected mice is no worse than the parental strain infected animal in the entire observation period.

Guinea Pig Safety Test

The safety of rBCG strains is also assessed in the guinea pig model in comparison to the parental BCG vaccine, which has a well-established safety profile in humans. First, the effect of the vaccine on the general health status of the animals is examined, including weight gain. Guinea pigs are immunized intramuscularly with $10^7$ (100× of vaccination dose) cfu of the recombinant and parental strains, and the animals are monitored for general health and body weight for six weeks. Post mortem examination is performed for animals that die before the six weeks period. All animals are sacrificed at the end of six weeks post infection and gross pathology is performed. There is no body weight loss, no abnormal behavior and all organs appear normal at the 6 week necropsy. A successful test is indicated when no adverse health effects are observed for rBCG-Pfo vaccine, and animals gain weight at the normal rate comparing with the parental strain inoculated animals.

At the same time, bacterial levels in animal organs are monitored. Guinea pigs immunized with either the parental or recombinant vaccine are euthanized at various intervals after inoculation, after which the lungs, spleens, and regional (inguinal) lymph nodes are assayed for cfu of BCG or rBCG.

Toxicity Test:

To evaluate the toxicity of the rBCG strains, guinea pigs 12 in each group are vaccinated intradermally with one dose, four times higher than the single dose or four times lower than the single dose of human use rBCG strains, BCG parental strain or saline respectively. At day three post vaccination, six animals are sacrificed to access the acute effects of the vaccine on these animals. At day 28 post vaccination, the remaining six animals are sacrificed to evaluate the chronic effects of on the animals. At both time points, the body weight of each animal is obtained, and gross pathology and appearance of the injection sites are examined. Blood is taken for blood chemistry, and the histopathology of the internal organs and injection sites are performed.

Studies to Determine Protection:

Murine Protection Study

C57B1/6 mice (female, 5-6 weeks of age) in groups of 13 will be immunized subcutaneously with $10^6$ CFU of rBCG, parental BCG or saline. Another group of mice is used as healthy controls. Eight weeks after immunization, mice are challenged with the M. tb Erdman strain (or H37Rv Kan-resistant strain) by an aerosol generated from a 10-ml single-cell suspension containing a total of $10^7$ CFU of the challenge strain, a dose that delivers 100 live bacteria to the lungs of each animal, as described previously. The experimental animals are monitored for survival along with unchallenged animals. Following the challenge, the animals are also monitored for weight loss and general health. At day one after challenge, three mice in each group are sacrificed for lung cfu to confirm challenge dose and one is sacrificed for spleen and lung histopathology. Then five weeks after challenge, nine animals in each group are sacrificed, and histopathology and microbiology analysis of the animal are performed. Lung and spleen tissues from six mice are evaluated for cfu counts (plates with selection supplements are used to distinguish the vaccine strain from the challenge strain). If challenged with H37Rv-kan resistant strain, Kan or TCH is used to distinguish the challenge strain from the vaccine strain. If the M. tb Erdman strain is used to challenge, TCH is used to distinguish the vaccine strain from the challenge strain (BCG is susceptible, but M. tb is naturally resistant).

Induction of Cutaneous Delayed-Type Hypersensitivity (DTH).

Specific pathogen free (SPF) guinea pigs will be immunized intradermally with $10^3$ rBCG or BCG parental strains. Nine weeks after immunization, the animals are shaved over the back and injected intradermally with 10 μg of PPD in 100 μl of phosphate buffered saline. After 24 hs, the diameter of hard induration is measured. rBCG strains should induce a DTH equal to or greater than that induced by parental BCG strains.

Guinea Pig Challenge Study

To determine the efficacy of the rBCG vaccines against M. tb challenge, guinea pigs are immunized (young adult SPF Hartley, 250-300 grams, male) in groups of 12, each with rBCG, parental BCG strain or saline. The vaccines and controls are administered intradermally with $10^6$ cfu. At 10 weeks after immunization, the rBCG-, BCG- and sham-immunized animals will be challenged by aerosol with the M. tb by an aerosol generated from a 10-ml single-cell suspension containing a total of $10^7$ cfu of M. tb ; this procedure delivers ~100 live bacteria to the lungs of each animal, as described previously (Brodin et al., J Infect Dis. 190(1), 2004). Following challenge, the animals are monitored for survival along with a healthy group of unvaccinated, unchallenged animals.

Following the challenge, the animals are monitored for weight loss and general health. Six animals in each group are sacrificed at 10 weeks post challenge and remaining six in each group at 70 weeks post challenge for long term evaluation. At both time points, histopathology and microbiology analysis of the animal will be performed. Lung and spleen tissues are evaluated for histopatholgoy and cfu count (plates with selection supplements are used to distinguish vaccine strain from challenge strain). If challenged with H37Rv-kan resistant strain, Kan or TCH is used to distinguish the challenge strain from the vaccine strain. If the M. tb Erdman strain is used to challenge, TCH (BCG is susceptible but M. tb is naturally resistant) is used to distinguish the vaccine strain from the challenge strain. Success is indicated when sham immunized animals die most rapidly after challenge, whereas the rBCG-immunized animals survive longer than the BCG parental strain immunized animals.

Primate Safety and Challenge Study:

More recently, the cynomolgus monkey has been used for evaluation of vaccines against M. tb . The evolutionary relationship between humans and non-human primates and the similar clinical and pathologic manifestations of tuberculosis in these species has made the non-human primate model attractive for experimental studies of TB disease and vaccine efficacy.

This model, characterized by the development of lung cavitation, appears to be applicable to human TB. The course of infection and disease is followed by X-ray and weight loss, as well as a variety of hematological tests, including erythrocyte sedimentation rate (ESR), peripheral blood mononuclear cell (PBMC) proliferation and cytokine production, cytotoxic T lymphocyte (CTL) activity, and antibody responses. Following infection, the cynomolgus monkey develops lung pathology with characteristic lesions, and, depending on the challenge doses, death from acute respiratory infection occurs within four-to six months after infection. Lower infection doses can lead to chronic infections without disease, much like in humans.

Study Design

The study will directly compare varying doses of the BCG parental strain versus recombinant BCG administered either alone or followed by two subsequent boosters with the vaccine comprising sequences that are overexpressed in the rBCG constructs. The latter could be delivered either as recombinant protein based in a suitable adjuvant formulation, DNA or Ad35 constructs.

The first study evaluates the protective efficacy of the parental BCG vs rBCG constructs without a booster. This study comprises three groups (10 animals each) designed as follows: one group each comprising BCG, rBCG and saline. Two animals from each group are skin tested with the overexpressed antigens in the rBCG constructs as well as with standard PPD and saline as controls. A positive and larger induration in the rBCG group compared with the BCG is indicative of in vivo vaccine take and the elicitation of an immune response. The remaining eight animals from each group are aerosol challenged with low dose M. tb Erdman strain and protection is measured by reduction of bacterial burden at 16 weeks post challenge or with survival as end point.

The follow up BCG prime protocol is essentially the same as above except that the animals are first vaccinated with BCG, rBCG and saline, followed by two boosters with the overexpressed antigens.

The immunogenicity and protection study in the non-human primate model will aim at investigating immunobiological and immunopathological aspects of tuberculosis in macaques for efficacy studies on rBCG constructs. The animals are juvenile to young adults raised in captivity with an average weight of 2 to 3 kg that have been thoroughly conditioned prior to the start of the experiment. Pre-inoculation studies consist of baseline blood tests that include routine hematological studies and erythrocyte sedimentation rates as well as lymphocyte proliferation assays. Skin testing is done with PPD to ensure lack of sensitivity to tuberculin and chest x-rays are obtained as part of the pre-infection profile. The immunization period will last 21 weeks in total, covering primary vaccination with BCG or rBCG at week=0 and antigen boosts at weeks 12 and 16. Antigen-specific immunity is assessed by measuring proliferation and interferon γ (IFNγ) secretion in lymphocyte stimulation tests. The frequency of IFNγ producing lymphocytes is determined by enzyme-linked immunosorbent assay (ELISPOT) or fluorescence-activated cell sorter (FACS). To this end, blood samples are drawn at weeks 0, 4, 8, 12, 16 and 20 weeks relative to primary vaccination.

Four to six weeks after the last immunization animals will be challenged by intratracheal installation of 3 ml (1,000 cfu) of the *M tuberculosis* Erdman on the same day and with the same preparation. The course of the infection will be assessed for weight loss, fever, elevated ESR, DTH to PPD, in vitro proliferative response of PBMC stimulated with PPD and the antigens over expressed in rBCG followed by measurements of the levels of IFN-g production. Chest x-ray will be performed to detect abnormalities consistent with pulmonary TB, and finally, necropsy will be carried out at 12-16 weeks post challenge.

Clinical Evaluation of TB Vectors and Vaccines

Safety and toxicity studies: Preclinical safety and toxicity studies as mandated by regulatory guidelines are performed as preclinical toxicology and safety studies as described above. Following these studies human safety studies are performed. These studies are performed initially in healthy Quantiferon negative adults, followed by age de-escalation into children and neonates.

Immunogenicity studies: Immunogenicity studies in mice and primates may utilize but are not limited to standard methods of evaluating cellular immunity such as INFγ, ELISPOT and/or flow cytometry with short and long term antigen or peptide stimulation. Similar methodologies are utilized for evaluation of human responses. Tetramer studies are employed for evaluation of CD4 and CD8 responses following vaccination of humans.

Optimization of prime-boost strategies: rBCG works well as a stand alone vaccine against TB or other diseases for which it has been engineered to express relevant transgenes. As used herein, a "transgene" is a DNA segment that is functionally linked to a mycobacterial promoter and expresses a protein of interest. rBCG as described here as a vaccine for TB or expressing transgenes to protect against other diseases also works extremely well to prime the immune system for booster immunization with recombinant proteins mixed with adjuvants or viral or bacterial vectored antigens. Both in animal preclinical studies and human studies the BCG prime followed by recombinant protein/adjuvant or vector boosts are optimized in terms of regimens and doses. These prime boost strategies are the most potent means for inducing immunity in humans because of the potency of the BCG prime especially as embodied in this invention followed by focusing and enhancing the booster response of the immune system by recombinant protein or vector.

Post-Exposure Therapeutic Vaccine Studies in Animals C57BL/6 mice will be used for establishing latent infection; therapeutic vaccines will be given to the mice at the time point when only negligible M. tb specific immunity has been induced by low dose infection and at another time point when M. tb specific immunity is subsided and predominated with memory T cells. The therapeutic benefit of the vaccines will then be assessed in mice two and five months after the last therapeutic vaccine delivery by enumerating cfu counts in lungs and spleens of individual mice. The cfu counts will be analyzed by standard statistical methods in the groups of mice and the results will be used to address whether therapeutic vaccination significantly reduces latent M. tb infection in mice. Similar methodologies are utilized for the evaluation of responses of other animals when necessary.

Clinical Evaluation of BCG Vectors: Oral Administration of rBCG Vaccines

Oral vaccination of the target animal with the rBCG of the present invention can also be achieved using methods previously described (Miller et al., Can Med Assoc J 121(1): 45-54; 1979). The amount of the rBCG administered orally will vary depending on the species of the subject, as well as the disease or condition that is being treated. Generally, the dosage employed will be about $10^3$ to $10^{11}$ viable organisms, preferably about $10^5$ to $10^9$ viable organisms.

The rBCG are generally administered along with a pharmaceutically acceptable carrier or diluent. The particular pharmaceutically acceptable carrier or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al, J. Clin. Invest., 79: 888-902; 1987; and Black et al., J. Infect. Dis., 155:1260-1265; 1987), or bicarbonate buffer (pH 7.0) containing ascorbic acid, lactose, and optionally aspartame (Levine et al, Lancet, II: 467-470; 1988). Examples of carriers include proteins, e.g., as found in skim milk, sugars, e.g., sucrose, or polyvinylpyrrolidone. Typically these carriers are used at a concentration of about 0.1-90% (w/v) but preferably at a range of 1-10% (w/v).

EXAMPLES

Example 1

Potency of Parent BCG Strains in Guinea Pigs:
Guinea Pig Protection Study with rBCG 30

As an example of a study conducted with the existing rBCG30 vaccine, a large guinea pig study was performed aimed at comparing the protective efficacy of two lots of rBCG30 with the parental BCG Tice strain itself and another commercially available BCG vaccine (SSI-1331 strain) used world wide in humans. The two rBCG30 lots were produced either under laboratory conditions (rBCG30-UCLA) or manufactured under GMP conditions (rBCG30-KIT) for human use.

Guinea pigs (10 animals per group) were immunized via the subcutaneous route with a single dose of $10^3$ cfu of each of the BCG vaccines. A negative control group (saline immunized) was included in the study. Eight weeks after the vaccination, the animals were challenged with the virulent Erdman strain via the aerosol route by calibrating the nebulizer compartment of the Middlebrook airborne-infection apparatus to deliver approximately 10-15 bacteria into the lungs. Animals were sacrificed at 10 weeks post challenge. At necropsy, lungs and spleens were removed from the animals and the number of viable bacteria determined by plating serial 10-fold dilutions of lung lobe and spleen homogenates onto nutrient Middlebrook 7H11. Bacterial colony formations were counted after 21 days of incubation at 37° C. under 5% (v/v) $CO_2$. Data are expressed as log10 of the mean number of bacteria recovered.

Figure 2:
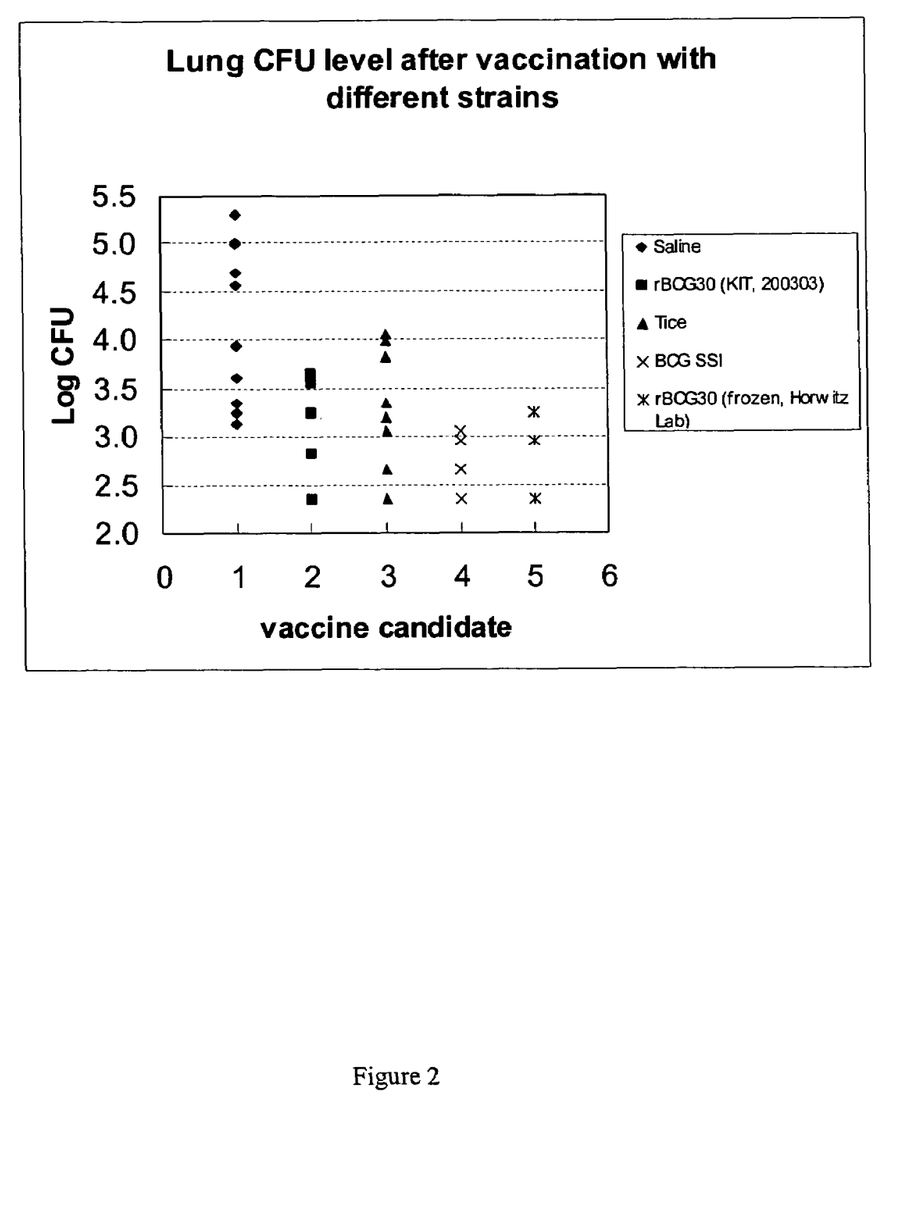
FIG. 2. Protection level measured by lung CFU amount after challenge for current different vaccine strains.
Figure 3:
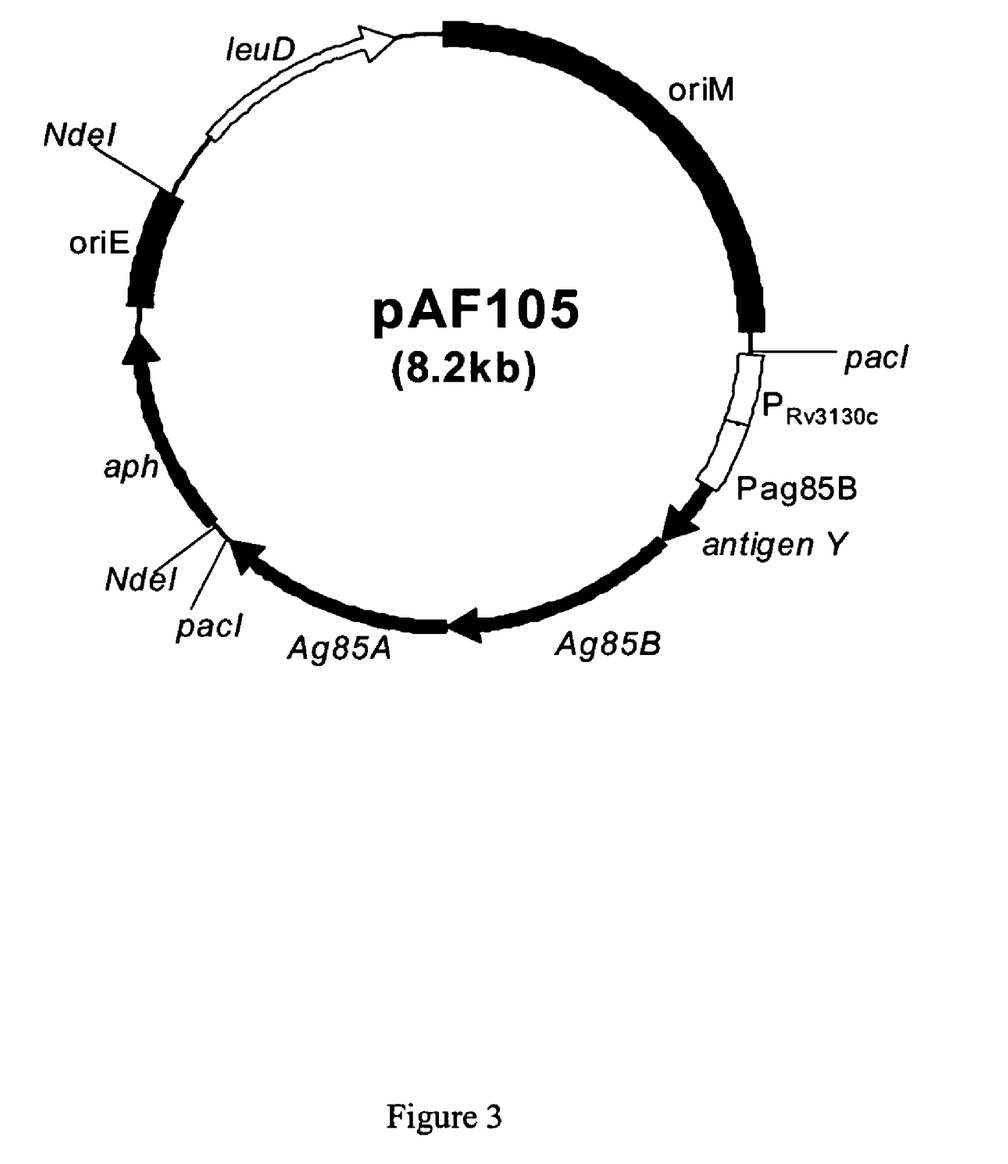

The results (FIG. 2) indicate that while all of the vaccines were protective against the Mtb challenge when compared with the negative, saline control, the differences between the vaccines trend into two groups with:
1) rBCG30 (UCLA), and BCG Danish 1331 being more protective; and
2) BCG (parental Tice strain) and rBCG30 (KIT) being less protective.

It is therefore reasonable to conclude that while rBCG30 (UCLA) produced under laboratory conditions, but not GMP grade, appears to induce better protection than the parental Tice strain, at best, the protective efficacy is only comparable with the commercially available BCG SSI. Therefore, an improvement on BCG Danish 1331 should be the objective of generating a new rBCG vaccine.

Example 2

Construction of Hosts to Serve as Carriers of Expression Vectors Devoid of Antibiotic-Resistance Markers Plasmid construction for knockout leuD gene in BCG Danish 1331 strain: The left and right 1 kb flanking regions of the leuD gene were assembled together by DNA synthesis (DNA 2.0, CA) to form a 2 kb DNA segment with pacI sites on both ends. This DNA fragment was cloned into the above mentioned allele exchange plasmid using PacI restriction enzyme digestion followed by ligation, to produce a leuD knockout plasmid.

Figure 4:
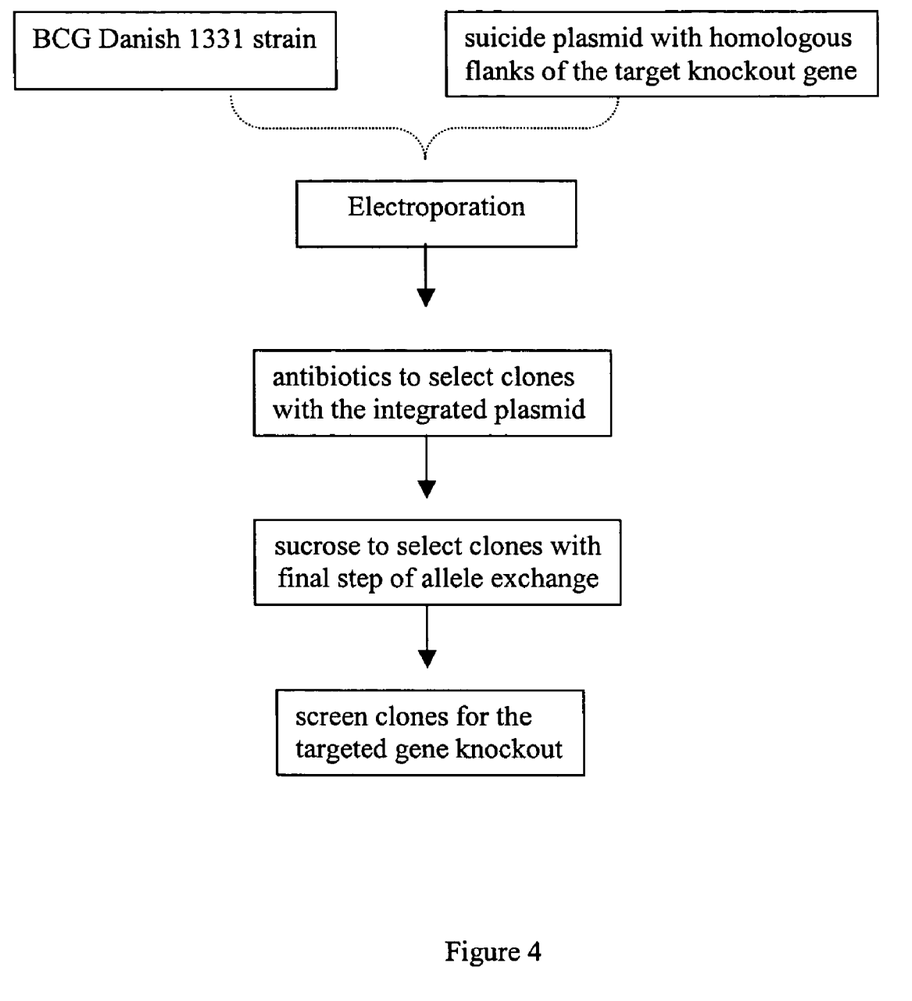
FIG. 4. Flow chart for the main steps of allele exchange.
Figure 5:
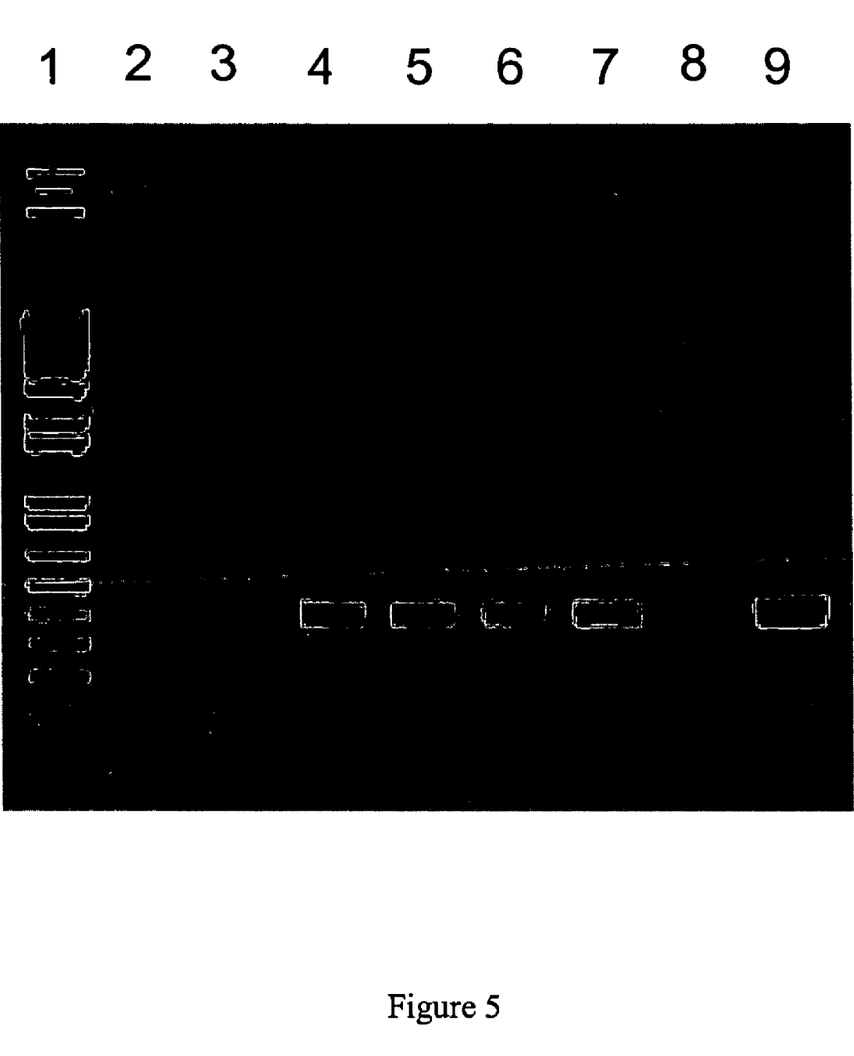

Allele exchange inactivation of the leuD gene: Inactivation of the leuD gene is carried out as described except 50 μg/ml of leucine will be supplemented in the culture medium for the strain with leuD gene knockout. A flowchart of the main steps of the procedure is given in FIG. 4.

Validation of LeuD Knockout:

Phenotypic test: The obtained strain is tested for its dependence on leucine supplement for growth. Specifically, the bacteria is cultured in the 7H9 medium with 10% OADC and 0.05% (v/v) Tyloxapol supplement in the presence or absence of 50 μg/ml of leucine, and the growth of the bacteria is monitored by measuring $OD_{600}$ value.

Genome regional sequence analysis: The genomic DNA of the constructed strain is prepared as previously described. Primer pairs complementary to both left and right 1 kb flanks of the targeted gene are used for PCR amplification to obtain a approximately 2 kb fragment from the chromosome. This PCR product is sequenced to confirm the absence of leuD gene in the region.

Example 3

Over-Expression of M. tb Antigens in rBCG Strains

DNA manipulations: The M. tb antigens TB10.4 (Rv0288), Ag85B (Rv1886c), and Ag85A (Rv3804c) are expressed polycistronically in the order described using promoters from Ag85B plus Rv3130 (Florczyk et al., supra, 2003). DNA sequences encoding a peptide with the sequence KDEL is placed at the end of each antigen as an endoplasmic reticulum retention signal to improve antigen presentation for each antigen. In addition, a 5'-loop structure and 3'-transcriptional terminator sequences are placed to ensure the stability of the transcribed polycistronic mRNA. Finally, restriction enzyme PacI sequences are used to flank both ends for ease in cloning the expression cassette into the expression vector. All DNA in the expression cassette is made by gene synthesis (Picoscript Inc, TX). The expression cassette is cloned into the expression vector by utilizing the PacI sites. After amplification in *E. coli*, the plasmid is digested with NdeI to eliminate oriE and the kanamycin resistance gene, followed by ligation to create a one-way shuttle system, which is then introduced into a *Mycobacterium* leuD auxotrophic mutant using standard electroporation procedures (Parish et al., Microbiology, 145: 3497-3503; 1999). FIG. 3 schematically depicts an exemplary non-antibiotic expression vector.

Expression of M. tb antigens using non-antibiotic selection system: The leucine autotrophy of BCG Danish 1331, which is used as the host for the non-antibiotic selection system, is cultured in 7H9 medium supplemented with 10% OAD (oleic acid-albumin-dextrose-catalase), 0.05% (v/v) Tyloxapol and 50 μg/ml of leucine. After electroporation, the recombinant strains harboring the antigen expression plasmid are isolated by plating on 7H10 plates (BD Difco) without leucine. The survival of the bacteria is dependent on the antigen expression of the leuD gene by the plasmid, which functions in turn as a mechanism to maintain the plasmid in the cells. The resultant individual colonies are isolated and cultured in 7H9 medium as above, except without leucine supplementation.

Validation of the expression: The expression of each antigen is detected by Western blot analysis. Specifically, the culture supernatant is collected and processed as previously described (Harth et al., Infect Immun 65(6):2321-2328; 1997). Then the expressed antigens are separated on an SDS-PAGE gel and blotted with antibodies to antigen 85A, 85B and 10.4. The expression level of each antigen is evaluated by quantitatively measuring the intensity of each specific band in comparison to that produced by expression plasmid negative host bacteria.

Example 4

Expressing the Selected Antigens in Mycobacteria without Antibiotic Selection Materials and Methods:

Plasmid and mycobacterium preparation for electroporation: The recombinant plasmid DNA was isolated and digested with the restriction endonuclease NdeI (New England Biolabs) to liberate the antibiotic-selection marker (e.g. kanamycin-resistance) and the *E. coli* origin of replication (OriE) region. Then, the digested plasmid DNA fragment was circularized using T4 DNA ligase (New England Biolabs) according to the manufacture's instructions. The resulting plasmid, which contains the *Mycobacterium* origin of replication and the selected antigens, but no antibiotic resistance gene and is not capable of replicating in Gram-negative bacteria, was introduced into the selected *Mycobacterium*. To prepare the *Mycobacterium* for electroporation, BCG Danish 1331 bacteria were cultured at 37° C. in Middlebrook 7H9 media (BD Biosciences) with 10% OADC supplementation to exponential growth phase. Tyloxapol (0.05% v/v, Research Diagnostics Cat. No. 70400) was used to disperse the bacteria. The cells were then washed in 10% glycerol plus 0.05% of Tyloxapol three times to remove the culture medium before electroporation. For each electroporation, 1.6 μg of plasmid was used for each $1.25\times10^8$ bacterial cells. The electroporation was carried out at 2.2 kV, 25 μF of capacitance and 1.0 kΩ of resistance. After the electroporation the cells were immediately plated on Middlebrook 7H10 agar (BD Biosciences) plates in 10-fold serial dilutions and incubated at 37° C.

PCR Screening of the Bacterial Colony Harboring the Expression Plasmid:

Recombinant strains were first screened by PCR using forward primer GTTAAGCGACTCGGCTATCG (SEQ ID NO: 1) and reverse primer ATGCCACCACAAGCACTACA (SEQ ID NO: 2) to amplify the DNA sequence of oriM region in an expression plasmid. The PCR parameters were as follows: Step 1: 95° C. 4 minutes, one cycle; Step 2: 95° C. 1 min, 60° C. 1 min, and then 72° C. 1 min for a total of 30 cycles; Step 3: 72° C. 10 minutes for one cycle. Step 4: 4° C. storage. The resultant PCR products were analyzed by agarose gel electrophoresis to verify the presence of the plasmid in the cells.

Results

A PCR that was designed to amplify the replication region of the plasmid (OriM) was performed to screen the resultant colonies for harboring the over-expression plasmid. Since this region is not present on the bacterial chromosome, the presence of this region in the cells is a strong indication that the plasmid has been introduced into the cells. Among the rBCG colonies screened, some colonies produced the PCR product, which is similar in size to that of a plasmid positive-control reaction, as analyzed by gel electrophoresis. In contrast, parental BCG bacteria did not produce any PCR product, as shown in FIG. 5. This experiment provides prima facie evidence that the plasmid has been successfully introduced into *Mycobacterium* and that a bacterial clone harboring the plasmid has been isolated without the use of antibiotic selection.

Discussion

Conventional plasmids for use in recombinant *Mycobacterium* strains contain a region of replication and a selection marker (normally an antibiotic-resistance gene, e.g. kanamycin-resistance or a gene that complements a metabolic defect, e.g. leuD or asd (Galan et al., Gene, 94:29; 1990) as essential plasmid elements that have utility in recombinant DNA experiments. Typically, antibiotics are used to select clones harboring recombinant plasmids. However, this poses a risk of the unintentional spread of antibiotic-resistance genes in instances where the antibiotic-resistant genetically modified organism is intended for use outside of laboratory containment.

In the study above, we introduced a recombinant plasmid capable of antigen expression, which contains neither the oriE region nor an antibiotic-selection marker into the bacteria and successfully isolated clones harboring the plasmid without using selection. Although the current experiment employed oriM as the plasmid replication region, it is envisaged that other plasmid replication regions will serve as substitutes, such as the replication region of pMF1 (Bachrach et al., Microbiol., 146:297; 2000). The unique advantage of this system is that the recombinant plasmid no longer possesses an antibiotic-resistance gene. Thus, it cannot inadvertently spread antibiotic resistance to the environment, as would be the case with commonly used expression plasmids. In addition, the one-way shuttle vector expression plasmid of the present invention is no longer capable of broad host range replication, since the genetic elements that enable such replication are deleted. This constraint adds a second level of containment to the recombinant plasmid, thereby substantially reducing the risks associated with release of a genetically modified (GMO) organism into the environment.

Although the current results show that it is possible to introduce recombinant plasmids into attenuated *Mycobacterium* strains without selection, other factors may be playing a role in the stability of the selection marker-free plasmid in the *Mycobacterium*. Thus, the replication region contains genes that facilitate plasmid replication and mediate plasmid segregation into sibling cells, thereby contributing to the ability to identify clones harboring the plasmid without selection.

A possible factor that enabled the isolation of clones harboring the plasmid without selection is that the higher plasmid to cell ratio used in the current approach. The use of a higher plasmid to cell ratio increases the probability that a cell will take in a plasmid, decreases the number of cells without plasmid. In this study, the plasmid to cell ratio was about 10 times higher than that typically utilized in conventional approaches that employ a selection system. In theory, even higher plasmid to cell ratios should result in even more clones harboring the plasmid, until a point of plasmid saturation is reached, which may inhibit intake of the plasmid DNA by the electroporated cells. In preferred embodiments of the invention, the ratio of plasmid to bacteria is in the range of about 0.5 μg to about 10 μg of plasmid DNA to about $1.25 \times 10^8$ bacterial cells, and preferably is in the range of about 1 μg to about 5 μg of plasmid DNA to about $1.25 \times 10^8$ bacterial cells.

In addition, the TB antigens that are over expressed by plasmid pAF105 may play an important role in plasmid stabilization. This plasmid over expresses two proteins of the antigen 85 complex (Ag85A (Rv3804c) and Ag85B (Rv1886c)), both of which possess a mycolyltranferase activity, which is required for the biosynthesis of trehalose dimycolate, a dominant structure necessary for maintaining cell wall integrity. It is possible, therefore, that over expression of at least one of these antigens contributes to the stability of the selection-free plasmid by conferring a growth advantage in the cells which harbor the plasmid, thus enabling identification of the clones that harbor the plasmid without selection.

We claim:

1. A transformed bacterium or progeny thereof which incorporates a nucleotide sequence, which replicates and is expressed therein, wherein said nucleotide sequence is not linked to a selectable marker, and wherein said nucleotide sequence resides on a plasmid, and wherein said nucleotide sequence encodes for a protein required for survival, and where a gene coding for said protein required for survival is deleted from bacterial genome of said transformed bacterium.

2. The transformed bacterium or progeny thereof of claim 1 wherein said transformed bacterium is auxotrophic.

3. The transformed bacterium or progeny thereof of claim 1 wherein said nucleotide sequence is at least a part of a one-way shuttle vector.

4. A transformed bacterium or progeny thereof which incorporates a foreign nucleotide sequence, which replicates and is expressed therein, wherein said foreign nucleotide sequence is not linked to a selectable marker, and wherein said foreign nucleotide sequence resides on a plasmid, and wherein said plasmid harbors a gene encoding for endosome escape.

5. The transformed bacterium or progeny thereof of claim 4 wherein said bacterium is a *Mycobacterium*.

6. A transformed bacterium or progeny thereof which incorporates a foreign nucleotide sequence, which replicates and is expressed therein, wherein said foreign nucleotide sequence is not linked to a selectable marker, wherein said foreign nucleotide sequence resides on a plasmid, and wherein said foreign nucleotide sequence codes for antigen 85a, antigen 85b, or antigen 85a/85b.

7. A transformed bacterium or progeny thereof which incorporates a foreign nucleotide sequence, which replicates and is expressed therein, wherein said foreign nucleotide sequence is not linked to a selectable marker, wherein said foreign nucleotide sequence resides on a plasmid, and wherein said plasmid harbors a gene encoding for proteins that maintain and/or stabilize the plasmid.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: synthetic oligonucleotide forward primer

<400> SEQUENCE: 1
gttaagcgac tcggctatcg                                              20

<210> SEQ ID NO 2
<211> LENGTH: 20
<212> TYPE: DNA
<213> ORGANISM: Artificial
<220> FEATURE:
<223> OTHER INFORMATION: synthetic oligonucleotide reverse primer

<400> SEQUENCE: 2
atgccaccac aagcactaca                                              20
```

8. The transformed bacterium or progeny thereof of claim 7 wherein said gene encoding for proteins codes for antigen 85a, antigen 85b, or antigen 85a/85b.

9. A transformed bacterium or progeny thereof which incorporates a foreign nucleotide sequence, which replicates and is expressed therein, wherein said foreign nucleotide sequence is not linked to a selectable marker, and wherein said foreign nucleotide sequence codes for apoptosis.

10. A transformed bacterium or progeny thereof which incorporates a foreign nucleotide sequence, which replicates and is expressed therein, wherein said foreign nucleotide sequence is not linked to a selectable marker, wherein said foreign nucleotide sequence resides on a plasmid, and wherein said plasmid harbors a gene encoding for apoptosis.

11. A transformed bacterium or progeny thereof which incorporates a foreign nucleotide sequence, which replicates and is expressed therein, wherein said foreign nucleotide sequence is not linked to a selectable marker, and wherein said foreign nucleotide sequence cannot be replicated in Gram negative bacteria.

12. A method of transforming a bacterium, comprising the step of incorporating a nucleotide sequence which replicates and is expressed in said bacterium, wherein said nucleotide sequence is not linked to a selectable marker, and wherein said nucleotide sequence resides on a plasmid, wherein said nucleotide sequence codes for a protein required for survival, and wherein a gene coding for said protein required for survival is deleted from bacterial genome of said bacterium.

13. The method of claim 12 wherein said step of incorporation is performed by electroporation.

14. The method of claim 12 wherein said nucleotide sequence is at least a part of a one-way shuttle vector.

15. A transformed *Mycobacterium* or progeny thereof comprising a foreign nucleotide sequence which encodes a protein of interest, and wherein said transformed *Mycobacterium* includes a plasmid that is incapable of replicating in Gram-negative bacteria.

16. The transformed *Mycobacterium* of claim 15 wherein said transformed *Mycobacterium* does not exhibit antibiotic resistance.

17. The transformed *Mycobacterium* of claim 15 wherein said transformed *Mycobacterium* is auxotrophic.

18. The transformed *Mycobacterium* or progeny thereof of claim 15 wherein said foreign nucleotide sequence is part of said plasmid.

19. The transformed *Mycobacterium* or progeny thereof of claim 18 wherein said plasmid lacks a selectable marker.

20. The transformed *Mycobacterium* or progeny thereof of claim 18 wherein said protein is required for survival and corresponds to a survival protein encoded by a nucleotide sequence deleted from bacterial genome of said transformed *mycobacterium*.

21. The transformed *Mycobacterium* or progeny thereof of claim 20 wherein said protein is leuD.

22. The transformed *Mycobacterium* or progeny thereof of claim 20 further comprising promoter sequences which are activated in vivo.

23. The transformed *Mycobacterium* or progeny thereof of claim 15 wherein said transformed *Mycobacterium* is attenuated.

24. The transformed *Mycobacterium* or progeny thereof claim 23 wherein said transformed *Mycobacterium* is BCG.

25. The transformed *Mycobacterium* or progeny thereof of claim 24 wherein said BCG is selected from the following strains BCG1331, BCG Pasteur, BCG Tokyo, and BCG Copenhagen.

26. A vaccine comprising a transformed *Mycobacterium* or progeny thereof comprising a foreign nucleotide sequence which encodes a gene of interest, and wherein said transformed *Mycobacterium* includes a plasmid which is incapable of replicating in gram-negative bacteria.

27. The vaccine of claim 26 wherein said transformed *Mycobacterium* does not exhibit antibiotic resistance.

28. The vaccine of claim 26 wherein said transformed *Mycobacterium* is auxotrophic.

29. A method of transforming a bacterium, comprising the step of incorporating a foreign nucleotide sequence which replicates and is expressed in said bacterium, wherein said foreign nucleotide sequence is not linked to a selectable marker, and wherein said foreign nucleotide sequence resides on a plasmid, wherein said foreign nucleotide sequence cannot be replicated in Gram negative bacteria.

* * * * *